(12) United States Patent
Weiss et al.

(10) Patent No.: US 6,574,425 B1
(45) Date of Patent: Jun. 3, 2003

(54) REFLECTOMETER

(75) Inventors: John Weiss, Mt. Sinai, NY (US); Irwin Weitman, East Northport, NY (US)

(73) Assignee: Jack L. Aronowitz, Pompano Beach, FL (US)

( * ) Notice: Subject to any disclaimer, the term of this patent is extended or adjusted under 35 U.S.C. 154(b) by 0 days.

(21) Appl. No.: 09/183,443

(22) Filed: Oct. 30, 1998

Related U.S. Application Data

(60) Provisional application No. 60/063,935, filed on Oct. 31, 1997.

(51) Int. Cl.[7] .................................................. G01J 3/50
(52) U.S. Cl. ..................... 386/402; 356/446; 250/214 B
(58) Field of Search ................................ 356/402, 420, 356/39, 445, 446; 435/14; 250/214 AL, 214 B

(56) References Cited

U.S. PATENT DOCUMENTS

| | | | |
|---|---|---|---|
| 3,910,701 A | 10/1975 | Henderson et al. | ........... 356/39 |
| 4,163,950 A | 8/1979 | Damm et al. | |
| 4,723,554 A | 2/1988 | Oman et al. | |
| 4,781,195 A | 11/1988 | Martin | ........................ 356/41 |
| 4,821,733 A | 4/1989 | Peck | |
| 4,935,346 A | 6/1990 | Phillips et al. | ................. 435/14 |
| 5,049,487 A | 9/1991 | Phillips et al. | ................. 435/14 |
| 5,059,394 A | 10/1991 | Phillips et al. | ................. 435/14 |
| 5,174,963 A | 12/1992 | Fuller et al. | ................. 356/446 |
| 5,179,005 A | 1/1993 | Phillips et al. | ................. 435/14 |
| 5,179,288 A | 1/1993 | Miffitt et al. | ................. 356/40 |
| 5,239,295 A | 8/1993 | DeLuca et al. | |
| 5,304,468 A | 4/1994 | Phillips et al. | ................. 435/14 |
| 5,426,032 A | 6/1995 | Phillips et al. | ................. 435/14 |
| 5,563,042 A | 10/1996 | Phillips et al. | ................. 435/14 |
| 5,843,692 A | 12/1998 | Phillips et al. | ................. 435/14 |

FOREIGN PATENT DOCUMENTS

| | | |
|---|---|---|
| EP | 0 426 967 | 9/1990 |
| EP | 0 477 417 | 9/1990 |
| WO | WO 83/00926 | 3/1983 |

OTHER PUBLICATIONS

PCT International Search Report, Mar. 15, 1999 PCT/US 98/23167.

*Primary Examiner*—F L Evans
(74) *Attorney, Agent, or Firm*—Saliwanchik, Lloyd & Saliwanchik

(57) ABSTRACT

A modulated light source emits light to illuminate a target surface which possesses a certain color and shade of color. Light that is reflected from the target surface is detected by an optical detector. The output from the optical detector is processed and fed back to the optical detector to compensate for any shift caused by ambient light, temperature or other external factors, and is differentially amplified to generate an output signal indicative of the color and shade of the target surface. The output signal from the differential amplifier is then demodulated by a synchronous detector to produce a substantially steady DC voltage that is indicative of the color or shade of color at the target surface. Where the target surface color shade is indicative of a certain measurable quantity or quality (such as an analyte concentration), the steady DC voltage is converted using a look-up table or mathematical formula into a corresponding quantity or quality measurement. In performing this conversion, compensation is made for any variations in modulated light source intensity due to temperature change.

27 Claims, 13 Drawing Sheets

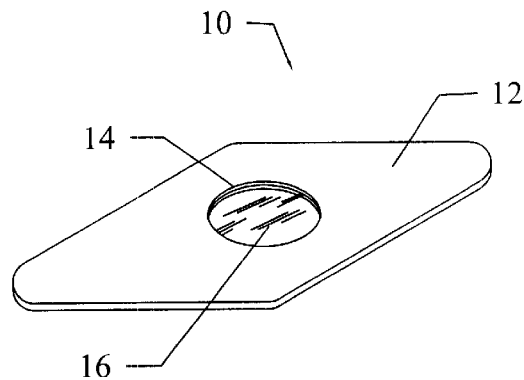
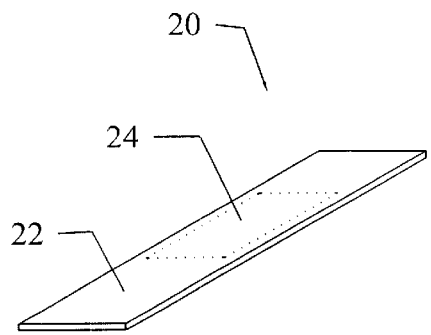
FIG. 1A
FIG. 1B
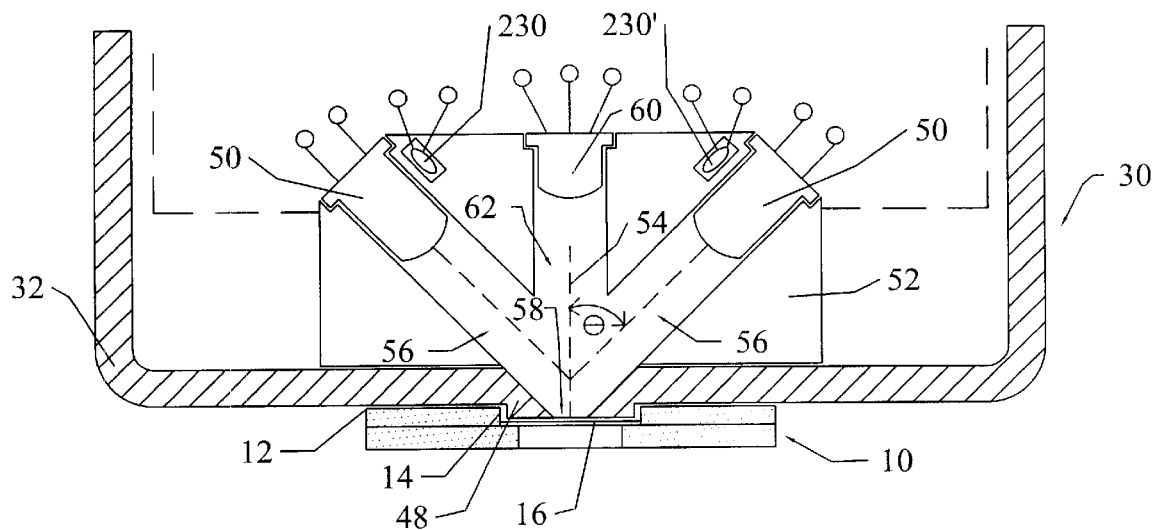
FIG. 3

| MV | mg/dL |
|---|---|
| 400 | 625 |
| 450 | 575 |
| 500 | 475 |
| 550 | 300 |
| 600 | 230 |
| 650 | 180 |
| 700 | 140 |
| 750 | 105 |
| 800 | 75 |
| 850 | 55 |

REFLECTOMETER

CROSS-REFERENCE TO RELATED APPLICATION

This application for patent claims priority from U.S. Provisional Application for Patent Serial No. 60/063,935, filed Oct. 31, 1997, and entitled "Reflectance-Type Glucose Meter."

BACKGROUND OF THE INVENTION

1. Technical Field of the Invention

The present invention relates to reflectometer technology and, in particular, to a method and apparatus for detecting and measuring color shades with a relatively high degree of accuracy. Where the color shades are indicative of a certain measurable quantity or quality, the present invention further relates to method and apparatus for converting the detected color shade into a corresponding quantity or quality measurement.

2. Description of Related Art

Presently, the only approved method for home monitoring of blood chemistry requires drawing blood by using a lance, usually by sticking a finger, and placing a drop of blood on a chemical strip. The resulting chemical reaction causes a change in the color of the strip with that change being read by a desk-top reflectance meter to provide an indication of blood sugar level. Another method also requires drawing blood, placing a drop of blood on a disposable printed circuit (PC) board, and measuring the electrical response of the blood to detect blood sugar level. Some attempts to use infrared techniques to look through the skin to make blood sugar determinations have proven to be less reliable and too expensive for commercial application.

Diabetics who need to control their insulin level via diet or insulin injection may test themselves five or six times per day, the frequency recommended by the American Diabetes Association. Some may choose to test less often than recommended to avoid the unpleasantness associated with drawing blood. There is accordingly a considerable amount of interest in the development of procedures for making blood sugar level determinations that avoid any need for inflicting injury to the patient.

One technology which has demonstrated accurate and repeatable results employs a transdermal patch to detect and measure blood sugar levels. This transdermal patch technology utilizes a transport mechanism to extract glucose related analytes from the skin (such as those found in interstitial fluid) for transport to a sensitive membrane. At this membrane, a chemical or biological reaction with the extracted analyte occurs to develop a color indicator thereon whose color and shade can be related to glucose levels. One such patch apparatus is disclosed by Aronowitz, et al., in commonly assigned, U.S. patent application Ser. No. 08/929,262, filed Sep. 11, 1997, the disclosure of which is incorporated herein by reference. Another patch-type glucose measurement technology is taught by Peck in U.S. Pat. No. 4,821,733, the disclosure of which is incorporated herein by reference.

With respect to at least that transdermal detection mechanism disclosed by Aronowitz, et al., the extracted analytes which are indicative of widely varying blood sugar levels unfortunately produce only very slight changes in developed color shade. In many instances, the difference between developed color shade for an acceptable and an unacceptable blood sugar level cannot be accurately and repeatably detected by the naked eye. To obtain the non-invasive benefits of transdermal glucose measurement technology while ensuring measurement accuracy in what may comprise a life critical testing procedure, it is therefore imperative that the fallible human activity of color shade evaluation and comparison be eliminated from the testing and measurement process.

There is accordingly a need for an ultra-sensitive meter capable of accurately resolving the full range of developed subtle color shade changes produced as a result of transdermal patch extraction and processing of certain analytes of interest. Preferably, the meter should be small, lightweight and portable (hand held). Beyond the obvious requirements for improved sensitivity to subtle differences in color shade, this meter should account for the effects of portability which are adverse to reading accuracy such as background light changes, temperature changes, and unsteady hand-held operation (for example, due to device pressure variation, rotation, and movement), and which are not normally associated with the desk-top meters that are widely employed for measuring blood sugar levels on test strips.

SUMMARY OF THE INVENTION

The present invention comprises reflectometer for detecting and measuring subtle changes in color and shade of color. In general, a pulsating light source illuminates a target surface which possesses a certain color and shade of color. An optical detection circuit synchronously detects light that is reflected from the target surface and generates an output signal whose voltage is indicative of the color and shade of the target surface. This voltage is then processed to make an evaluation and identification of any measurable quantity or quality that is represented by the detected color or shade of color.

More specifically, a modulated light source emits light to illuminate the colored target surface, where the specific color or shade of color is indicative of a certain measurable quantity or quality (such as an analyte concentration). The modulated light that is reflected from the target surface is detected by an optical detector. The output signal from the optical detector is differentially amplified to produce an AC output signal indicative of the color and shade of the target surface. The output signal from the optical detector is further processed and fed back to the optical detector to compensate for any shift in the DC level of the AC output signal caused by the detection of ambient light or the influence of other external factors. The output signal from the differential amplifier is then demodulated by a synchronous detector to produce a substantially steady DC voltage that is indicative of the color or shade of color at the target surface. This DC voltage is converted to a corresponding digital value, and that digital value is converted using a look-up table or other mathematical formula into a corresponding quantity or quality measurement.

BRIEF DESCRIPTION OF THE DRAWINGS

A more complete understanding of the method and apparatus of the present invention may be acquired by reference to the following Detailed Description when taken in conjunction with the accompanying Drawings wherein:

FIGS. 1A and 1B are perspective views, of a transdermal patch and a testing strip, respectively, which each develop a color shade indicative of the detected presence within the patient of an analyte of interest;

FIG. 3 is a cross-sectional view of the sensor head of the hand-held reflectometer shown in FIGS. 2A and 2B;

DETAILED DESCRIPTION OF THE DRAWINGS

Figure 2A:
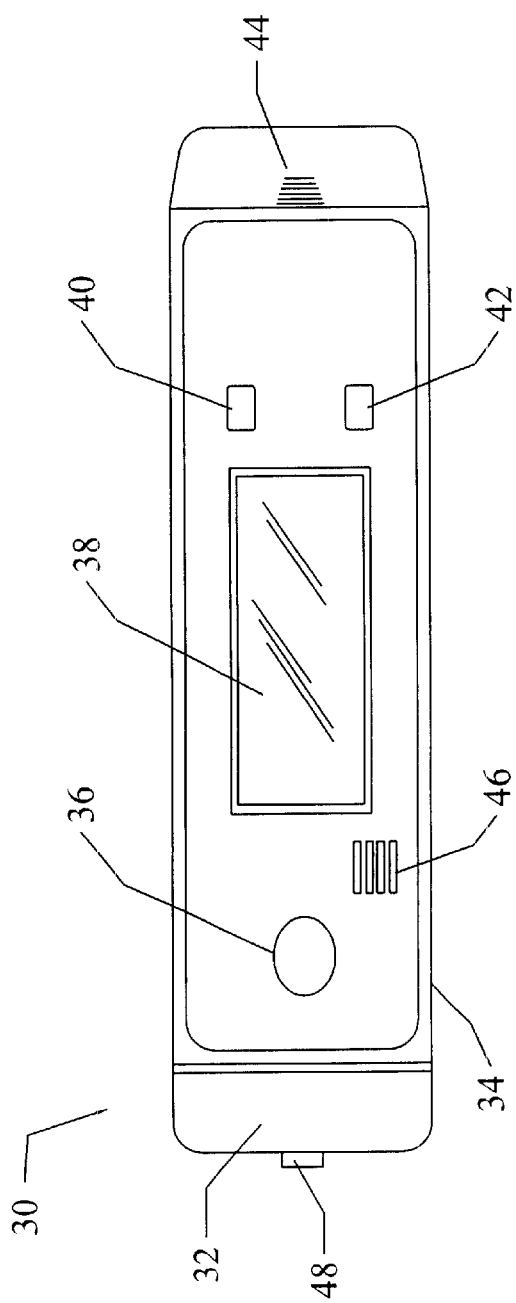
FIGS. 2A and 2B are top and side views, respectively, of a hand-held reflectometer suitable for reading developed color shade on the transdermal patch of FIG. 1A.

Reference is now made to FIG. 1A wherein there is shown a perspective view of a transdermal patch 10 which develops a color shade indicative of the detected presence within the body of an analyte of interest (and perhaps also its concentration). The patch 10 has a rounded rectangular shape (as shown), but may also have other shapes as desired (such as round or oval). A top surface 12 of the patch 10 includes a generally circular opening 14 which exposes a membrane 16 to view. In general, a bottom surface (not shown) of the patch 10 includes an adhesive layer and may be affixed to the skin of a patient. A certain analyte of interest is then extracted from the skin and transported through a gel-like transport medium to the membrane 16. At the membrane 16, a biological and chemical reaction occurs with respect to the extracted analyte of interest to develop a color indicator thereon which is indicative of the presence within the body of the analyte. The shade of the developed color indication may also be indicative of analyte concentration level within the body. As an example, the analyte of interest may relate to blood sugar, and thus the developed color shade on the membrane would be indicative of glucose level. Other analytes of interest could be extracted by the patch 10 and used to develop color indications on the membrane 16 related to cholesterol, triglycerides, bilirubin, creatinine, urea, alpha-amylase, L-lactic acid, alanine aminotransferase (ALT/GPT), aspartate aminotransferase (AST/GOT), albumin, uric acid, fructose amine, potassium, sodium, chloride, pyruvate dehydrogenase, phenylalaninehydroxylase, purine nucleotide enzymes and phenylalanine hydroxylase or its substrates such as phenylalanine, phenyl-pyruvate or phenyl-lactate, to name a few. More detailed explanation of transdermal patch construction and operation may be obtained by reference to commonly assigned, U.S. Pat. application Ser. No. 08/929,262, filed Sep. 11, 1997, the disclosure of which is incorporated herein by reference.

Reference is now made to FIG. 1B wherein there is shown a perspective view of a testing strip 20 which develops a color shade indicative of the presence within the body of an analyte of interest (and perhaps also its concentration). The strip 20 has a generally rectangular shape. A top surface 22 of the strip 20 includes a testing region 24. In general, a drop of bodily fluid (such as blood, urine, saliva, perspiration, and the like) is deposited on the testing region 24. A biological and chemical reaction occurs with respect to an analyte of interest within the deposited fluid to develop a color indicator on the stip 20 indicative of the presence within the body of the analyte. The shade of the developed color indication may also be indicative of analyte concentration level within the body. As an example, the analyte of interest may relate to blood sugar, and thus the developed color shade on the strip 20 would be indicative of glucose level. Other analytes of interest (such as those discussed above with respect to the transdermal patch 10) could be processed in the testing region 24 and used to develop color indications related to analyte concentrations.

Figure 2B:
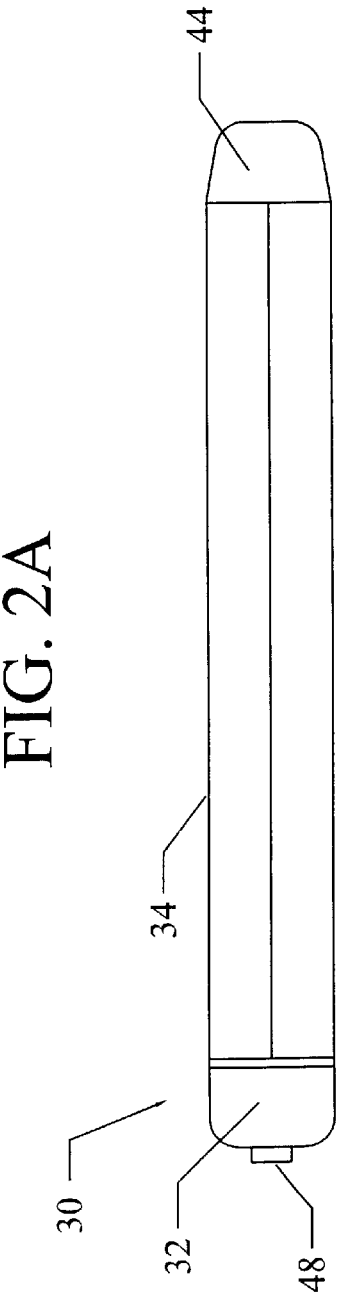

Reference is now made to FIGS. 2A and 2B wherein there are shown top and side views, respectively, of a hand-held reflectometer 30 suitable for reading developed color and shade on the transdermal patch 10 of FIG. 1A. The reflectometer 30 includes a sensor head 32 on one end of a semi-cylindrical case 34 that can be comfortably held in one hand. A "READ" button 36 activates the reflectometer 30 to make a measurement of color and shade at the sensor head 32. A liquid crystal display (LCD) 38 provides numerical output to a user of the reflectometer 30 that is indicative of the color shade (such as for example, a voltage level) or of some measurable quantity or quality related to that read color shade (such as, for example, a concentration level). The display 38 may also provide other important information to the user such as date and time of day. If the display 38 is capable of producing alphabetic and/or graphic as well as numeric characters, the display may also be used to provide messages to the user (perhaps relating to instructions for use, error indications, icons, reminders, and the like). Two key switches, a "SCROLL" button 40 and a "SELECT" button 42, are located on the face of the reflectometer 30. Utilizing these buttons 40 and 42, the user may set date and time of day information. These buttons 40 and 42 may further be utilized to program alarms which alert the user as to when it is necessary to take a reading. The user may still further utilize the buttons 40 and 42 to enter data into the reflectometer 30 that is necessary to ensure accurate measurement and information output. As an example, the user may select a manufacturing batch code for the transdermal patch 10, or input color/shade data for calibrating the reflectometer 30, or select the type of testing to be performed (for example, glucose versus cholesterol). A battery compartment 44 is located in the top end of the meter. An external port connection (not shown) may also be provided to allow the user to connect the reflectometer 30 up to a personal computer or a telephone line or an infra-red communications link in order to communicate readings. The reflectometer 30 further includes an opening 46 for a speaker (not shown) that may produce sounds such as alarm sounds and data entry confirmation sounds.

Operation of reflectometer 30 may be better understood by presentation of the following example of its use with a transdermal patch 10 such as that illustrated in FIG. 1A. Once applied to the skin, the transdlermal patch 10 requires approximately a three to five-minute incubation period (dependent on number of factors including temperature). As an example, the transdermal patch 10 is preferably attached to the skin on the inside of the patient's forearm. Once the transdermal patch 10 is applied to the skin, the user may depress the SELECT button 42 to start a user chosen, reflectometer calculated or pre-programmed count-down period which measures the time required for incubation and development of the color shade indicative of extracted analyte. After the time expires, an audible alarm alerts the user that it is now time to take a reading. A cylindrical shaped protruding nose portion 48 of the sensor head 32 (generally matching in size and shape the circular shape of the opening 14) is then inserted into the opening 14 of the transdermal patch 10 and positioned adjacent the membrane 16. The user then depresses the "READ" button 36 to power up the device and initiate reflectometer 30 operation to detect and measure any developed color and shade present on the membrane 16. Data such as a signal voltage level relating to the detected color shade or an analyte concentration relating to the detected color shade is then output for user consideration on the display 38. Alternatively or additionally, this data may be output through the external port connection for remote processing and analysis to inform the user of analyte concentration information.

Reference is now made to FIG. 3 wherein there is shown a cross-sectional view of the sensor head 32 of the hand-held reflectometer 30 shown in FIGS. 2A and 2B. The sensor head 32 contains a dual light source to increase the reflective signal strength and to more uniformly illuminate the target surface of the membrane 16 where the color and shade indicative of analyte presence and concentration level is developed. Two light emitting diodes (LEDs) 50 are mounted in a housing 52 at a certain angle Θ to normal 54 with respect to the membrane 16. The LEDs 50 may be of any suitable color related to the color shades to be detected. As an example, red LEDs 50 with a wavelength of approximately 637 nm have been found to produce excellent results in detecting the color shades which develop on the membrane 16 from the use of an appropriate chromophore or fluorophore indicator (such as O-Tolidine, tetra-methyl benzine, and the like) during glucose analyte testing. LEDs of other colors (such as green) or perhaps infra-red may be used (perhaps in conjunction with the red LEDs) depending on the selected chromophore or fluorophore indicator. The housing 52 is constructed with a low-expansion plastic such as Ryton, preferably with a non-reflective surface, and should be opaque as to the wavelength of the light source to substantially eliminate any background signal from stray reflection of light emitted from the LEDs 50. The angle Θ may be any angle that minimizes detection of specular reflection and is preferably approximately forty to forty-five degrees. The LEDs 50 each have a relatively narrow (for example, fifteen degree) projection angle with respect to their emitted light output. The light output from the LEDs 50 is directed along a light pipe (or collimator) 56 through an opening 58 in the protruding nose 48 portion of the sensor head 32 to illuminate the target surface. The position of the LEDs 50 along the length of the light pipe 56 may be adjusted during fabrication of the reflectometer to alter the intensity of target surface illumination and the effects and instances of side reflections within the light pipe. A photo transistor 60 is mounted within the housing 52 and oriented along the normal 54 with respect to the target surface of the membrane 16 for the transdermal patch 10. The photo transistor 60 similarly has a relatively narrow (for example, fifteen degree) viewing angle. Reflected light emitted from the target surface of the membrane 16 passes through the opening 58 in the protruding nose 48 portion of the sensor head 32, and is directed along a light pipe (or collimator) 62 to the photo transistor 60. The position of the photo transistor 60 along the length of the light pipe 62 may be adjusted during fabrication of the reflectometer to alter the sensitivity and tolerance of the reflectometer in reading target surface illumination and color shade. Arrangement of the LEDs 50 and photo transistor 60 in the illustrated angle Θ offset and symmetrical orientation serves to. minimize detection of specular reflection off the target surface of the membrane 16 and reduce the effect of rotational error about the normal 54 that may result from a slightly uneven illumination of the target surface,.

Figure 4:
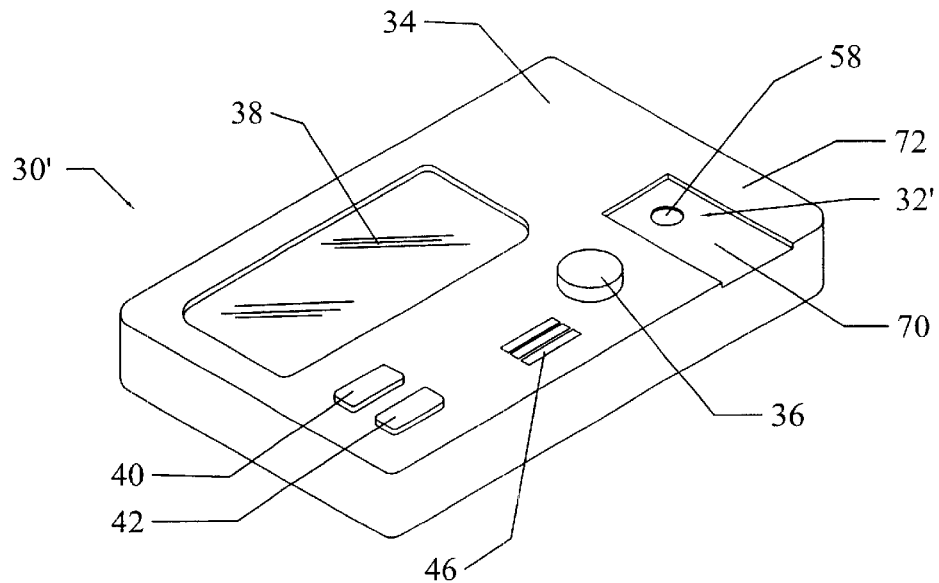
FIG. 4 is a perspective view of a desk-top reflectometer suitable for reading developed color shade on the testing strip of FIG. 1B.

Reference is now made to FIG. 4 wherein there is shown a perspective view of a desk-top reflectometer 30' suitable for reading developed color shade on the testing strip 20 of FIG. 1B. The reflectometer 30' includes a reading site 32'. A "READ" button 36 activates the reflectometer 30' to make a measurement of color shade at the reading site 32'. A liquid crystal display (LCD) 38 provides numerical output to a user of the reflectometer 30' that is indicative of the detected color shade or of some measurable-quantity or quality related to that read color shade. The display 38 may also provide other important information to the user such date and time of day. If the display 38 is capable of producing alphabetic and/or graphic as well as numeric characters, the display may also be used to provide messages to the user (perhaps relating to instructions for use, error indications, icons, reminders, and the like). Two key switches, a "SCROLL" button 40 and a "SELECT" button 42, are located on the face of the reflectometer 30'. Utilizing these buttons 40 and 42, the user may set date and time of day information. These buttons 40 and 42 may further be utilized to program alarms which alert the user as to when it is necessary to take a reading. The user may still further utilize the buttons 40 and 42 to enter data into the reflectometer 30' that is necessary to ensure accurate measurement and information output. As an example, the user may select a manufacturing batch code for the testing strip 20, or input color/shade data for calibrating the reflectometer 30', or select the type of testing to be performed (for example, glucose versus cholesterol). An external port connection (not shown) may be provided to allow the user to connect the reflectometer 30' up to a personal computer or a telephone line or an infra-red communications link in order to communicate readings. The reflectometer 30' further includes an opening 46 for a speaker (not shown) that may produce sounds such as alarm sounds and data entry confirmation sounds.

Operation of reflectometer 30' may be better understood by presentation of the following example of its use with a testing strip 20 such as that illustrated in FIG. 1B. The reflectometer 30' is activated and recognizes from detected voltage level whether a testing strip is in place within a slot 70. If not, the reflectometer 30' prompts the patient to insert a strip. Responsive to insertion of a testing strip into the slot 70, the reflectometer 30' prompts the patient to deposit a sufficient amount of bodily fluid (such as blood, urine, saliva, perspiration, and the like) is then deposited on the testing region 24 of the strip 20. A biological and chemical reaction occurs with respect to an analyte of interest within the deposited fluid to develop a color indicator on the strip 20 whose shade can be related to analyte concentration levels. A timer is then initiated to measure whether sufficient progress in the chemical reaction (based on detected voltage level) occurs within a predetermined first time period (that may be user chosen, reflectometer calculated or pre-programmed). If not, the patient is prompted to start the testing process over with a new strip. If sufficient progress occurs within this first time period, the timer then starts measuring a second time period (that may be user chosen, reflectometer calculated or pre-programmed) to detect completion of the testing process. In one supported testing procedure, expiration of the second time period initiates reflectometer 30' operation to detect and measure color shade on the strip 20. Data such as a signal voltage level relating to the developed color shade or an analyte concentration relating to the developed color shade is then output for user consideration on the display 38. In another supported testing procedure, the reflectometer 30' operates to measure a voltage level indicative of detected color shade on the strip 20. If the measured voltage level stabilizes before expiration of the second time period, data such as a signal voltage level relating to the developed color shade or an analyte concentration relating to the developed color shade is then output for user consideration on the display 38. Alternatively or additionally, the data may be output through the external port connection for remote processing and analysis to inform the user of analyte concentration information. In the event that either 1) the measured voltage level does not stabilize, or 2) the measured voltage level drops below an acceptable threshold, an error message is displayed to prompt the patient to start the testing process over with a new strip.

Figure 5:
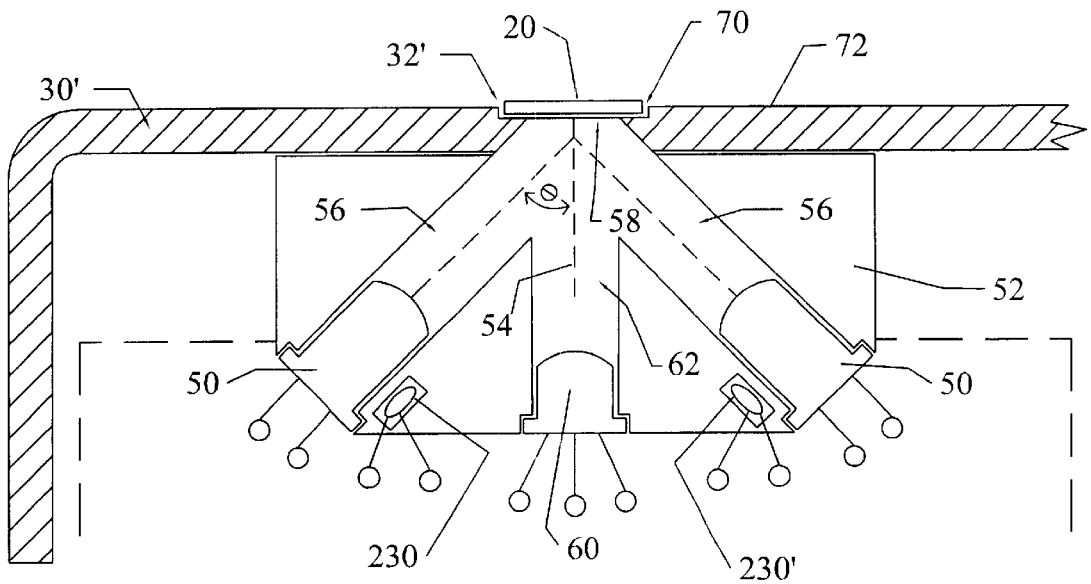
FIG. 5 is a cross-sectional view of the reading site of the desk-top reflectometer shown in FIG. 4.

Reference is now made to FIG. 5 wherein there is shown a cross-sectional view of the reading site 32' of the desk-top reflectometer 30' shown in FIG. 4. The reading site 32' contains a dual light source to increase the reflective signal strength and to more uniformly illuminate the target surface of the strip 20. Two light emitting diodes (LEDs) 50 are mounted in a housing 52 at a certain angle Θ to normal 54 with respect to the strip 20. The LEDs 50 may be of any suitable color related to the color shades to be detected. As an example, red LEDs 50 with a wavelength of approximately 637 nm have been found to produce excellent results in detecting the color shades which develop on the strip 20 from the use of an appropriate chromophore or fluorophore indicator during cholesterol analyte testing. LEDs of other colors (such as green) or perhaps infra-red may be used (perhaps in conjunction with the red LEDs) depending on the selected chromophore or fluorophore indicator. The housing 52, is constructed with a low-expansion plastic such as Ryton, preferably with a non-reflective surface, and should be opaque as to the wavelength of the light source to substantially eliminate any background signal from stray reflection of light emitted from the LEDs 50. The angle Θ may be any angle that minimizes detection of specular reflection and is preferably approximately forty to forty-five degrees. The LEDs 50 each have a relatively narrow (for example, fifteen degree) projection angle with respect to their emitted light output. The light output from the LEDs 50 is directed along a light pipe (or collimator) 56 through an opening 58 in the top 72 of the reflectometer case along the slot 70. The position of the LEDs 50 along the length of the light pipe 56 may be adjusted during fabrication of the reflectometer to alter the intensity of target surface illumination and the effects and instances of side reflections within the light pipe. A photo transistor 60 is mounted within the housing 52 and oriented along the normal 54 with respect to the target surface of the strip 20. The photo transistor 60 similarly has a relatively narrow (for example, fifteen degree) viewing angle. Light emitted from the target surface of the strip 20 passes through the opening 58, and is directed along a light pipe (or collimator) 62 to the photo transistor 60. The position of the photo transistor 60 along the length of the light pipe 62 may be adjusted during fabrication of the reflectometer to alter the sensitivity and tolerance of reflectometer in reading target surface illumination and color shade. Arrangement of the LEDs 50 and photo transistor 60 in the illustrated angle Θ offset and symmetrical orientation serves to minimize specular reflection off the target surface of the strip 20 and reduce any adverse effects arising from a slightly uneven illumination of the target surface.

Figure 6A:
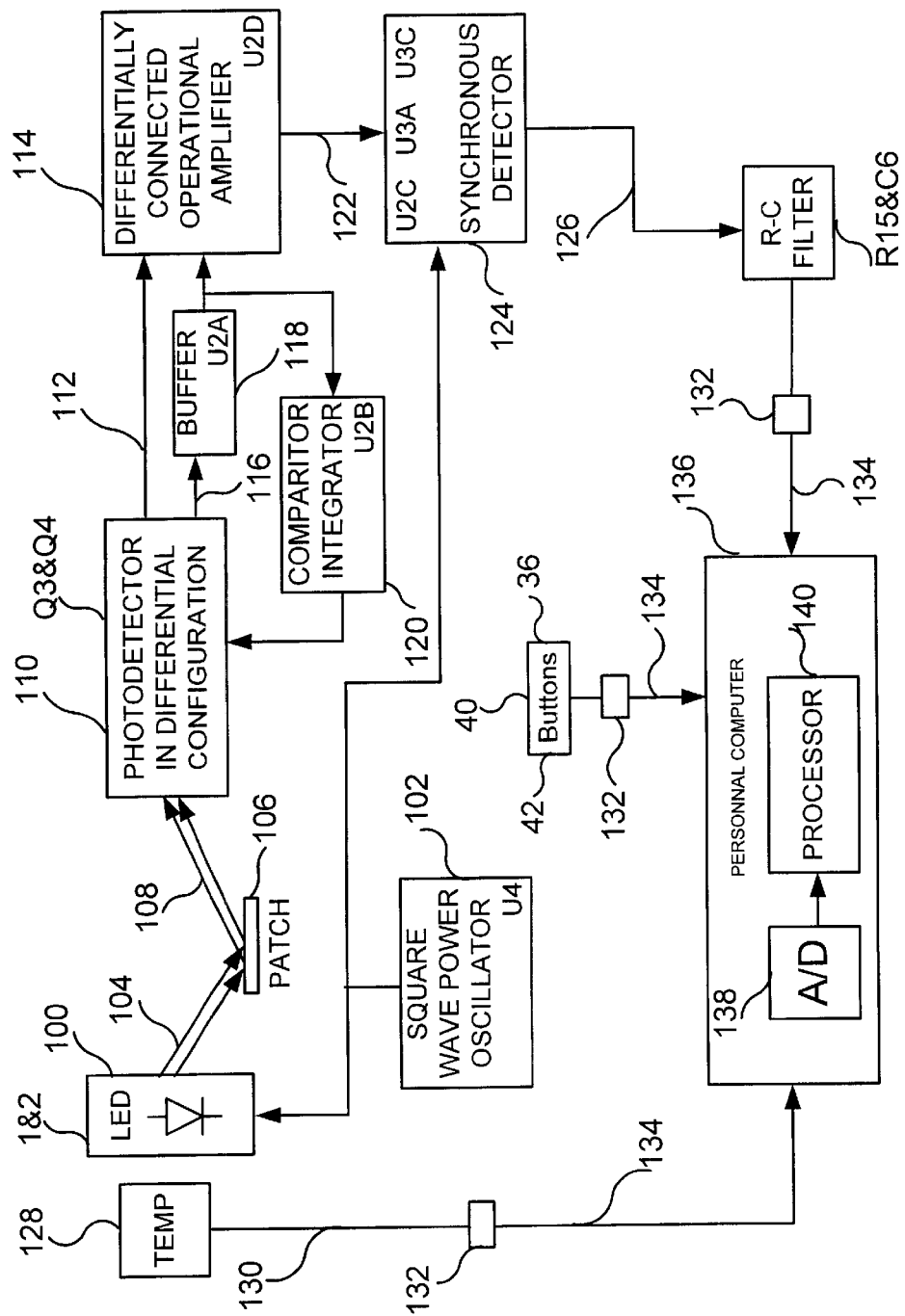
FIGS. 6A and 6B are block diagrams of an electronic circuit for two embodiments of a reflectometer in accordance with the present invention.
Figure 6B:
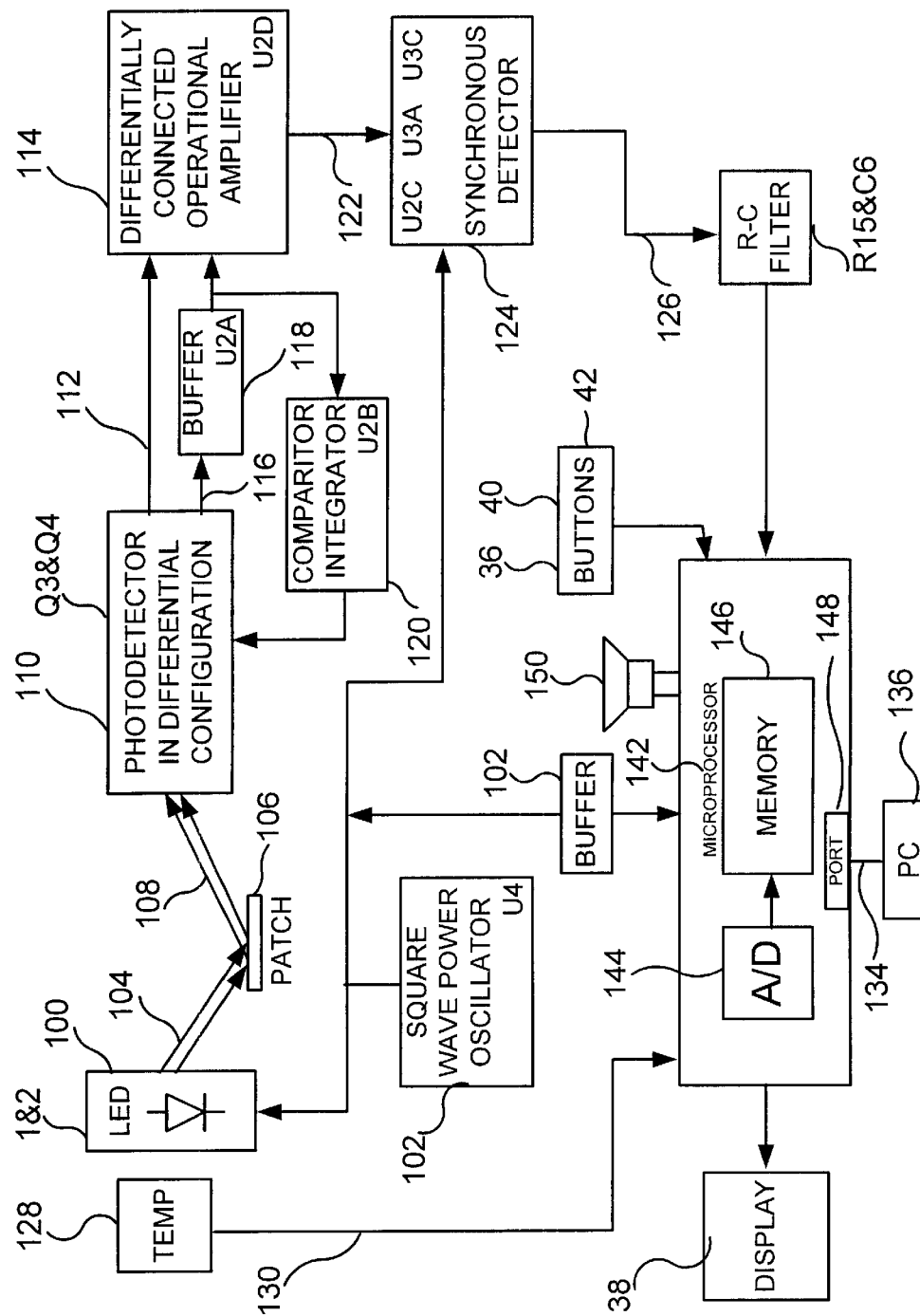

Reference is now made to FIGS. 6A and 6B wherein there are shown block diagrams for two embodiments of an electronic circuit for the reflectometer 30/30' in accordance with the present invention. A light source 100 is driven by a square wave current to emit pulses of light 104 which illuminate a target surface 106. In one embodiment (shown in FIG. 6A) the square wave is generated by an oscillator 102. In another embodiment (shown in FIG. 6B) the square wave is generated by a microprocessor 142. As shown in FIGS. 3 and 5, the light source may comprise a pair of LEDs 50 of the same or different colors. In situations where different colors are used, the LEDs may be pulsed either simultaneously or alternately. The pulses of light 104 are output from the light source 100 with a frequency of seventy-five Hertz and a duty cycle of fifty percent. Any frequency may be chosen provided it does not comprise a harmonic or sub-harmonic of AC line voltage (i.e., fifty or sixty Hertz), and is sufficiently high enough to read the target surface and allow for a statistically significant number of reflectivity samples to be taken within an acceptably short measurement period. The target surface 106 that is illuminated by the light source 100 may comprise, for example, the membrane 16 of a transdermal patch 10 like that shown in FIG. 1A or the surface of a strip 20 like that shown in FIG. 1B. Alternatively, any other substrate may be illuminated by the light source 100.

The illuminated target surface 106 reflects the received light 104 and thus radiates light 108 corresponding to the developed color and shade on the target surface 106 which is detected by an optical detector 110. As shown in FIGS. 3 and 5, the optical detector 110 may include a photo transistor 60. The optical detector 110 generates in a differential amplifier configuration a pair of differential outputs 112 and 116 (one-hundred and eighty degrees out of phase from each other) whose peak-to-peak voltages are representative of the detected color and shade of the target surface 106. The pair of differential outputs 112 and 116 are applied to a differential (to unbalanced conversion) amplifier 114 to generate a single output signal 122 whose peak-to-peak voltage is representative of the detected color and shade of the target surface 106. The second output 116 of the optical detector 110 is applied to a buffer 118 before being applied to the differential amplifier 114. The buffer 118 output is also applied to an integrator 120 which compares the signal to a reference voltage and integrates the result of the comparison to generate a DC signal 162 to bias the optical detector 100 back to its designed quiescent operating point and thus compensate for any detected ambient (DC) background light. The output 122 of the differential amplifier 114 accordingly provides a signal whose peak to peak voltage level is indicative of the color and shade of the target surface (when the light source is illuminated) as opposed to any color or shade that relates to the effects of ambient DC light at the target surface (when the light source is off).

The output 122 of the differential amplifier 114 is then applied to a synchronous detector 124. The synchronous detector 124 also receives the light source 100 drive signal which is output from the oscillator 102 and obtains information concerning when the light source 100 is illuminating (and not illuminating) the target surface. As this illumination is being detected by the optical detector 110, and since the signal output 122 from the differential amplifier 114 is affected by the detected illumination, the synchronous detector 124 may then process the output 122 to full wave rectify the signal output 122 from the differential amplifier 114 and produce a substantially steady DC voltage that is indicative of the color or shade of color at the target surface. The output 126 from the synchronous detector 124 is then low pass filtered to remove any included high frequency components resulting from the synchronous detection process before any subsequent processing occurs.

Positioned adjacent to the light source 100 (perhaps with some included thermo-mechanical coupling) is a temperature sensor 128. The temperature sensor 128 generates an output 130 that is indicative of temperature at or near the light source. This information is important to consider in situations where the brightness and intensity of the light 104 emitted from the light source 100 varies with changes in temperature. Any experienced brightness or intensity changes in the emitted light 104 cause corresponding changes in the output signal 126. With knowledge of temperature indicative information, appropriate actions can be taken during subsequent processing of the signal 126 output from the synchronous detector 124 in order to account for the temperature driven variations in emitted light and the corresponding variations in the output signal 126.

Reference is now specifically made to FIG. 6A. In accordance with a first embodiment of the present invention, the previously described components of the reflectometer 30/30' are contained within a case (such as the hand held or desk top units described above). The ireflectometer 30/30' outputs the signal 126 and the signal 130 through an external port connection 132 and over a communications link 134 to a personal computer 136 (separate and apart from the case for the reflectometer 30/30') where the signal are processed. The communications link 134 may comprise, for example, multi-wire cable if the reflectometer 30/30' is proximately located to the personal computer 136, or a telephone line or infra-red transceiver if the reflectometer is remotely located to the personal computer 136. A PC/MCIA card (not shown) may be utilized to interface the reflectometer 30/30' to the personal computer 136. It will, of course, be understood that suitable equipment (not shown but well known to those skilled in the art) must also be included to interface the reflectometer 30 to a telephone line. In the personal computer 136, the received signals 126 and 130 are converted by a internal digital-to-analog converter 138 to digital values.

These digital values are then processed by an internal processing unit 140 to generate information concerning analyte concentration level. The detected concentration information is then displayed by the personal computer 136 on its display screen and stored in computer memory for later retrieval, consideration, analysis and transfer. In this embodiment, the signals output from the "READ" button 36, "SCROLL" button 40 and "SELECT" button 42 (see, FIG. 2A) of the reflectometer 30/30' are also transmitted through the external port connection 132 and over the communications link 134 to the personal computer 136.

Reference is now specifically made to FIG. 6B. In accordance with a second embodiment of the present invention, all the required reading and processing components of the reflectometer 30/30' are advantageously contained within a case (such as the hand held or desk top units described above). This provides for a self-contained, portable device. The signal 126 and the signal 130 are presented to a microprocessor 142 located within the reflectometer 30/30' case. The microprocessor 142 includes an analog-to-digital conversion functionality 144 for converting the analog signals 126 and 130 to digital values. These digital values are then processed by the microprocessor 142 to generate information concerning detected analyte concentration level. The detected concentration information is then displayed by the reflectometer 30/30' on the liquid crystal display 38 and stored in the microprocessor 142 memory 146 for later retrieval, consideration and transfer. An external port connection 148 is provided through the microprocessor 140 in order to allow for the communication of the detected concentration information over a communications link 134 to a personal computer 136. The communications link 134 may comprise, for example, multi-wire cable if the reflectometer 30/30' is proximately located to the personal computer 136, or a telephone line if the reflectometer is remotely located to the personal computer 136. Preferably, the microprocessor 142 includes the appropriate circuitry for interfacing the reflectometer 30/30' to a telephone line. As an alternative, the microprocessor 142 may utilize the light source 100 to allow for the communication of the detected concentration information over an optical communications link (such as an infra-red connection). In this embodiment, the processor appropriately modulates the light source with the detected concentration information to effectuate a data communication.

The "READ" button 36, "SCROLL" button 40 and "SELECT" button 42 (see, FIG. 2A) are connected as inputs to the microprocessor 142. Using the "READ" button 36, the user activates the reflectometer 30/30' to make a measurement of color shade. The liquid crystal display 38 then provides a numerical output to the user that is indicative of the color shade or of some measurable quantity or quality related to that read color shade. Using the "SCROLL" button 40 and "SELECT" button 42, the user may set date and time of day information, request current date and time of day information, program alarms which alert the user as to when it is necessary to take a reading, enter reflectometer data (such as a manufacturing batch code for the transdermal patch 10, or input color/shade data for calibrating the reflectometer), and select the type of testing to be performed (for example, glucose versus cholesterol). A speaker 150 is connected to the microprocessor 142 to provide audible signals to the user (such as an alarm).

Figure 7A:
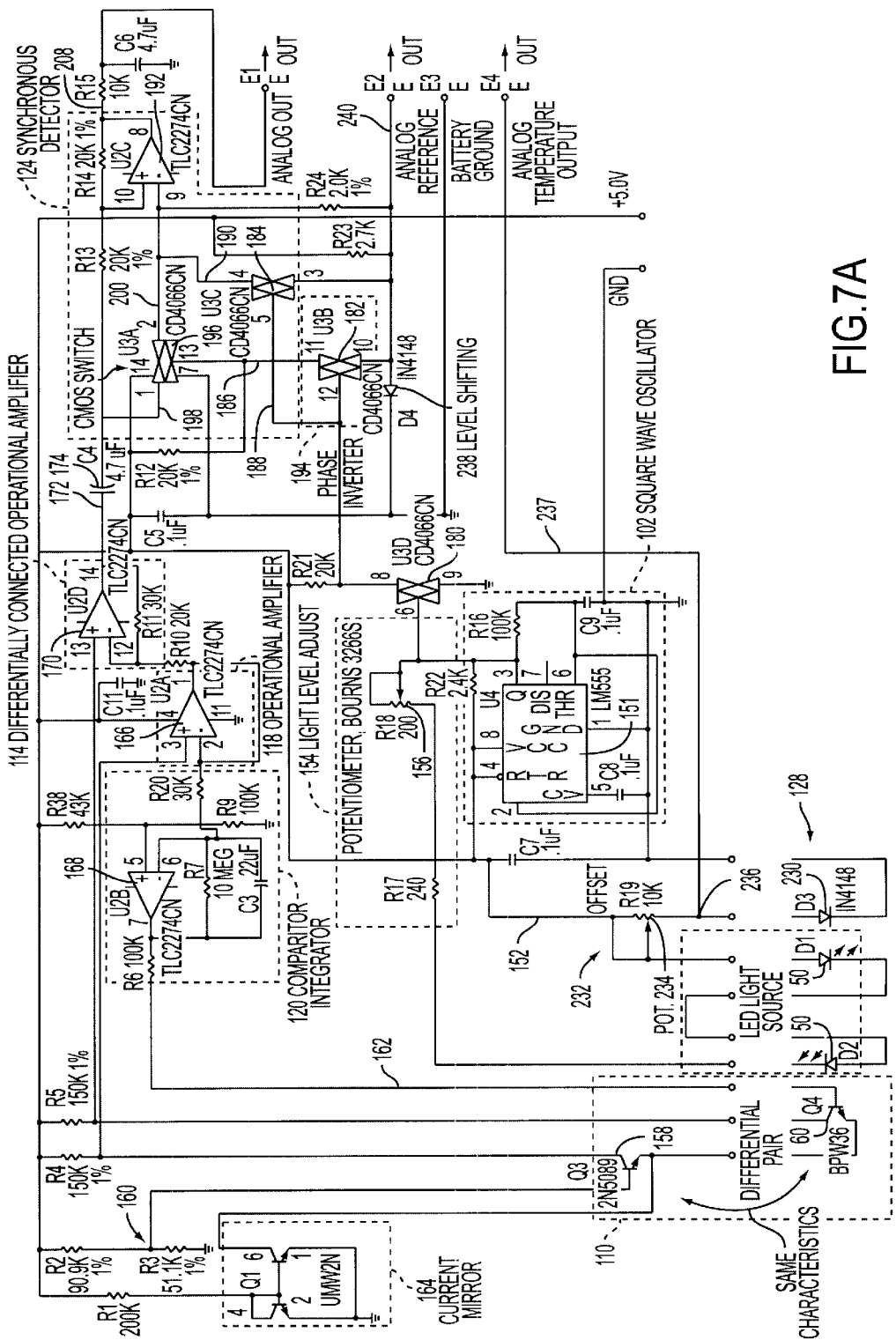
FIGS. 7A and 7B are circuit diagrams for an analog portion of the reflectometer of the present invention as shown in FIGS. 6A and 6B, respectively.
Figure 7B:
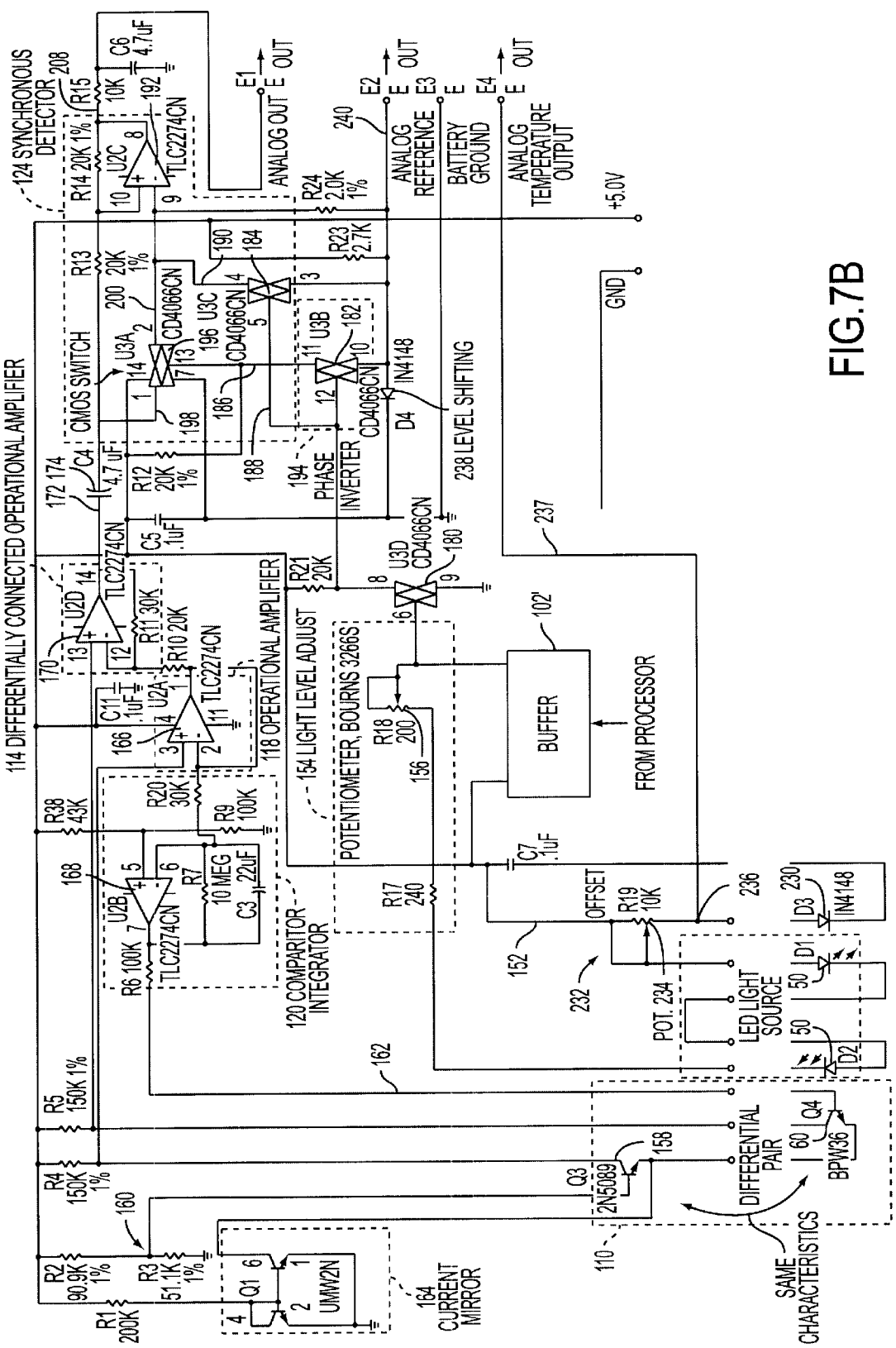

Reference is now made to FIGS. 7A and 7B wherein there are shown circuit diagrams for an analog portion of the reflectometer of the present invention (as illustrated in FIGS. 6A and 6B, respectively). The square wave oscillator 102 in the embodiment of FIG. 6A comprises a conventional LM555 timer integrated circuit 151 configured with appropriately connected resistors and capacitors to generate a square wave output on line 152 at a selected frequency (for example, seventy-five Hertz) and with a selected duty cycle (for example, fifty percent). Alternatively, the square wave is generated by the microprocessor 142 in the embodiment of FIG. 6B and supplied by a buffer 102' for output on line 152. The square wave output on line 152 is applied to a pair of series connected LEDs 50 (which emit pulses of light) and a light level adjustment circuit 154 comprising a potentiometer 156 within the light source 100.

The adjustment provided through use of the potentiometer comprises a factory performed adjustment to set the level or intensity of pulsed light output from the LEDs 50 for the reflectometer 30/30'. More specifically, the adjustment comprises a first order calibration of the reflectometer 30/30'. A more complete explanation of how this calibration process is executed is provided below.

The modulated light is reflected from a target surface and detected (with minimal spectrally reflected components) by the optical detector 110. This optical detector 110 includes a photo transistor 60 differentially connected to another transistor 158, wherein the differentially connected photo transistor and other transistor share substantially similar operating characteristics. By differential connection it is meant that the emitters of the photo transistor 60 and the transistor 158 are connected to each other. The base of the transistor 158 is driven by a signal output from a voltage divider circuit 160 to set the quiescent operating point of the detector 110. The base of the photo transistor 60 is driven by a feedback signal (to be described in more detail below) on line 162 in order to bias the photo transistor back to the optimum quiescent operating point (and thus account for the detection of ambient DC light). A current mirror circuit 164 supplies a fixed constant current to the connected emitters of the photo transistor 60 and the transistor 158 in the differential connection.

The photo transistor 60 generates a first differential output signal 112 at its collector. The transistor 158 generates a second differential output signal 116 at its collector. The first and second differential output signals 112 and 116 are one hundred eighty degrees out of phase with each other and each have a peak to peak voltage that is representative of detected light (including its color and shade) which is reflected from the target surface. The second differential output signal 116 is applied to a buffer 118 comprising a voltage follower connected operational amplifier 166. The signal 116 output from the buffer 118 is applied to the integrator 120 which comprises an integrator connected operational amplifier 168. The integrator 120 makes a comparison of the buffered signal 116 to a DC reference voltage, and integrates the result of that comparison to generate the feedback signal on line 162 whose voltage is proportional to a detected error between the desired quiescent operating point of the optical detector 110 and an average voltage shift therein caused by ambient (DC) light detected by the photo transistor 60, temperature variations in the differential pair and other external factors (like component aging). The generated feedback signal on line 162 is then applied to the base of the photo, transistor. 60 to bias the component back to the preferred quiescent operating point and thus account for these external factors (in the peak to peak voltages of the generated first and second differential output signals 112 and 116) which would otherwise result in measurement errors with respect to the color and shade detection of the reflected pulsed light emitted from the light source 100.

The first and second differential output signals 112 and 116 are applied to the differential amplifier 114 comprising a differentially connected operational amplifier 170. The differential amplifier 114 subtracts the first differential output signal from the second differential output signal to provide a single output signal 122 on line 172 having a peak to peak voltage that is representative of detected light (including its color and shade) which is reflected from the target surface. Any DC components within this output signal 122 are removed by a DC blocking capacitor 174. The remaining AC components (comprising generally speaking a square wave whose peak to peak voltage is proportional to the reflected light detected by the photo transistor 60 and representative of the color and shade characteristics of that light) is then applied to the synchronous detector 124.

The synchronous detector 124 receives the square wave signal output from the square wave oscillator 102 and uses it to perform a synchronous full wave rectification of the output signal 122 (demodulation) to produce a substantially steady DC voltage indicative of the color or shade of color at the target surface. This synchronous detection process further functions to eliminate any shifts in the output signal 122 caused by ambient (AC) light (for example, from fluorescent light) detected by the photo transistor 60. More specifically, the synchronous detector 124 functions to produce the substantially steady DC voltage which accurately measures the peak to peak AC voltage of the output signal 122 derived from the optical detector without being subject to any DC effects.

The synchronous detector 124 includes an operational amplifier 192 that is selectively configured, based on the received square wave signal, to provide for either inverting or non-inverting unity gain processing of the output signal 122. This functionality is provided through the actions of a plurality of CMOS switches. A first CMOS switch 180 buffers and phase inverts the square wave signal, and drives a second CMOS switch 182 and a third CMOS switch 184. The second CMOS switch 182 functions as a phase inverter, such that the first and second CMOS switches generate square wave output signals on line 186 and 188 that are one-hundred eighty degrees out of phase with each other. One of those signals (line 188) is applied to the third CMOS switch 184, and the other one of the signals (line 186) is applied to a fourth CMOS switch 196. The third CMOS switch 184, when activated by the line 188 signal, connects the non-inverting input of the operational amplifier 192 to a reference ground supplied by diode 238. The fourth CMOS switch 196, when activated by the line 186 signal, connects the non-inverting input of the operation amplifier 192 to receive the DC blocked output signal 122. The output signal 122 is further provided to the inverting input of the operational amplifier 192.

When the third CMOS switch 184 is activated, the fourth CMOS switch 196 is not activated. Due to the grounding of the non-inverting terminal, the operational amplifier 192 is configured to provide for unity gain inverted processing of the output signal 122. Conversely, when the third CMOS switch 184 is activated, the fourth CMOS switch 196 is not activated. Due to the lifting of the ground and the connection of the output signal 122 to the non-inverting and inverting terminals, the operational amplifier 192 is configured to provide for unity gain non-inverted processing of the output signal 122. By appropriately phasing the square wave signal application to control CMOS, switch activation, a synchronous full wave rectification of the output signal 122 is provided.

Figure 8A:
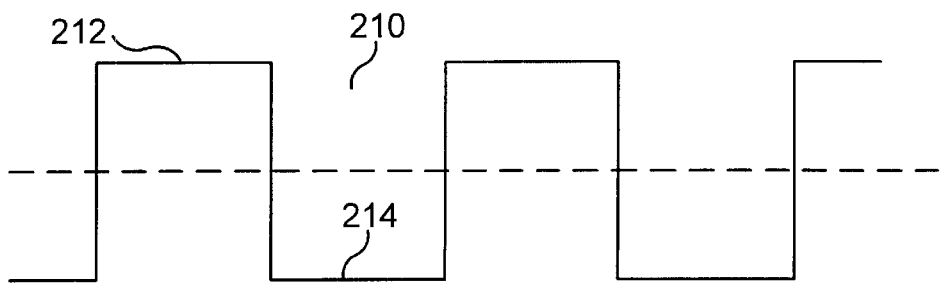
FIGS. 8A and 8B are waveform diagrams illustrating operation of a synchronous detector of the present invention.
Figure 8B:
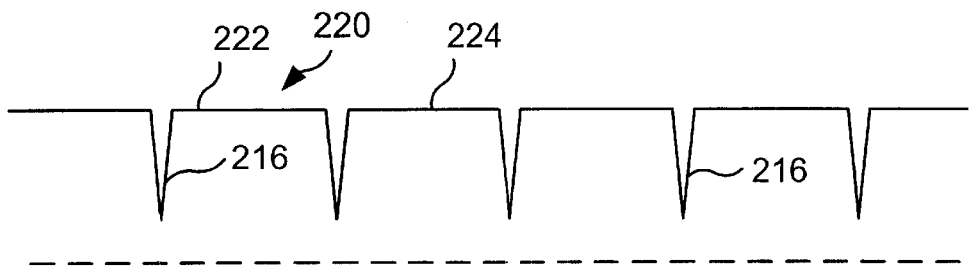

Operation of the synchronous detector 124 of the present invention to provide for synchronous full wave rectification may be better understood by reference to FIGS. 8A and 8B. In FIG. 8A, there is shown the waveform 210 for the output signal 122 as received by the synchronous detector 124. The waveform 210 includes a positive portion 212 and a negative portion 214 with a peak to peak voltage that is indicative of the color or shade of color at the target surface. Responsive to the square wave signal (correctly phased), the third CMOS switch is activated to ground the non-inverting terminal, and the operational amplifier 192 thus is configured to provide non-inverting unity gain processing of the output signal 122 during the positive portion 212. Next, again responsive to the square wave signal (correctly phased), the fourth CMOS switch is activated to connect the output signal 122 to the non-inverting terminal and the operational amplifier 192 thus is configured to provide inverting unity gain processing of the output signal 122 during the positive portion 214. The switching of the third and fourth CMOS switches continues as driven by the square wave signal. The result of this selective processing is to generate the output signal 126' on line 208, as shown in FIG. 8B, having a substantially steady DC voltage indicative of the color or shade of color at the target surface. The waveform 220 includes a first portion 222 corresponding to the non-inverted (positive) portion 212 of the output signal 122, and a second portion 224 corresponding to the inverted (negative) portion 214 of the output signal 122. It is noted that the waveform 220 still further includes a slight negative spike 216 at each point where the output signal from the square wave oscillator 102 switches between low and high due to the CMOS switch effects.

With reference now once again to FIG. 7, the output signal 126 on line 208 is filtered by an R-C first order low pass filter to remove the slight negative spikes 216 within the waveform 220. The resulting filtered output signal 126 is then provided as a first analog signal output from the analog portion of the reflectometer 30/30' for subsequent digital processing (see, FIGS. 6A and 6B).

The diode 238 introduced DC level shift affects the DC voltage level of the output signal 126 from the synchronous detector (and hence the first analog signal output from the analog portion of the reflectometer 30/30'). The DC level shift therefore must be accounted for in order to ensure that the output first analog signal is properly interpreted to detect color and shade at the target surface. More specifically, the DC level shift must be subtracted from the output signal 126. Thus, the DC level shift voltage is output on line 240 as a second analog signal output from the analog portion of the reflectometer 30/30' for subsequent digital processing. This may be performed during digital processing or, alternatively, taken care of in the analog portion of the reflectometer 30/30' by utilizing a differential amplifier (not shown) to perform the subtraction of the second analog signal from the first analog signal prior to any subsequent digital processing.

As discussed above, the reflectometer 30/30' further includes a temperature sensor 128. It is recognized that the LEDs 50 are temperature sensitive components with respect to their light output. In order to be able to accurately track operational changes due to temperature variation, the temperature sensor 128 preferably comprises a diode 230 (having operational characteristics complementing those of the LEDs 50) thermo-mechanically coupled to the LEDs 50 and electrically connected between ground and the line 152 square wave output from the oscillator 102 through a level adjustment circuit 232 comprising a potentiometer 234. This adjustment comprises a factory performed adjustment to set a level for the temperature indicative voltage output from node/line 236. The temperature indicative voltage on line 236 thus comprises a third analog signal output from the analog portion of the reflectometer 30/30' for subsequent digital processing.

Reference is now once again made to FIGS. 6A and 6B. The first analog signal output (after subtracting the second analog signal output) and the third analog signal output from the analog portion of the reflectometer 30/30' are next digitally processed. More specifically, the DC voltage of the first analog signal representative of the detected reflected light at the target surface (and indicative of color and shade) is analog-to-digital converted to a first digital value. Similarly, the DC voltage of the third analog signal representative of temperature is analog-to-digital converted to a second digital value. The first and second digital values are then processed to calculate a compensated voltage that directly relates to the color and shade of the non-spectral reflectance off the target surface at standard conditions. The processor, by use of a stored lookup table that correlates a certain compensated voltage (indicative of target surface color and shade) to a certain analyte concentration, or through the use of an appropriate mathematical formula, identifies an analyte concentration level output value. The user selection of reflectometer data (such as a manufacturing batch code for the transdermal patch 10 or testing strip 20) and type of testing to be performed (for example, glucose versus cholesterol) identifies which one of a plurality of stored lookup tables or formulae should be considered by the processor in evaluating the compensated voltage indicative of target surface color and shade to determine the corresponding analyte concentration level output value.

As discussed briefly above, the intensity of the light output from the LEDs 50 is affected by ambient temperature. As temperature increases, the intensity of the light output decreases. Conversely, as temperature decreases, the intensity of the light output increases. Accounting for any temperature changes at the light source is thus imperative in order to ensure that the detected steady DC voltage is an accurate representation of color and shade.

A number of different temperature sensing mechanisms may be utilized. In accordance with a first one of those mechanisms, it is recognized that the LEDs 50 are diodes, and that the diode 230 may be advantageously used as a temperature sensor which mimics the temperature sensitive operation of the LEDs. The voltage drop across the diode is affected by temperature in the same way the light intensity output from the LEDs 50 is affected by temperature. With a measurement of this voltage drop in comparison to a reference voltage drop at a known temperature, it is possible to determine current temperature.

As an example, the temperature dependance of the voltage drop ($V_{dc}$) of a small signal diode (such as 1N4148) is measured to be approximately 0.0021 volts/degree C. At factory calibration of the reflectometer 30/30', the forward voltage drop across the diode 230 is set by adjustment to the potentiometer 234 to, for example, 0.609 volts at twenty-five degrees C. Once this baseline voltage drop is established, any measured difference between the actual voltage drop and the baseline voltage drop can be easily converted into a temperature variation, and that determined temperature variation accounted for in evaluating both the operation of the LEDs 50 and the first analog output signal.

In this regard, it is noted that the temperature effect on the light intensity output from the LEDs 50 varies with the detection signal nearly linearly over the limited temperature range of interest with respect to the reflectometer 30/30'. A plot of the temperature error in volts versus the reflectance (i.e., the first analog signal representative of the detected reflected light at the target surface and indicative of color and shade) accordingly reveals a substantially straight line that intersects the origin and has a positive slope of substantially 0.0035 volts/degree C (hereinafter k1). The voltage adjustment (ΔV) that must be made to account for changes in temperature from a standard may be calculated as follows:

$$\Delta V = k1 \times SV \times \Delta C$$

wherein: SV is the signal representative of the detected reflected light at the target surface and indicative of color and shade; and ΔC is the sensed temperature change (i.e., detected offset) from a reference standard of twenty-five degrees C, and is equal to:

$$\Delta C = \frac{V_{dt} - V_{dr}}{V_{dC}}$$

wherein: $V_{dt}$ is the currently measured voltage drop across the diode; and $V_{dr}$ is the voltage drop across the diode at a reference standard of twenty-five degrees C.

The compensated voltage CV (which accounts for the effects of temperature) may be calculated through the use of standard mathematical manipulations, the compensated voltage may be calculated as follows:

$$CV = SV \times (1 - k2 \times (V_{dt} - V_{dC}))$$

wherein: k2 is a constant equal to $k1/V_{dC}$.

In the case of the specific example signal diode mentioned above, k2 equals 0.0035/0.0021=1.667.

Figure 9A:
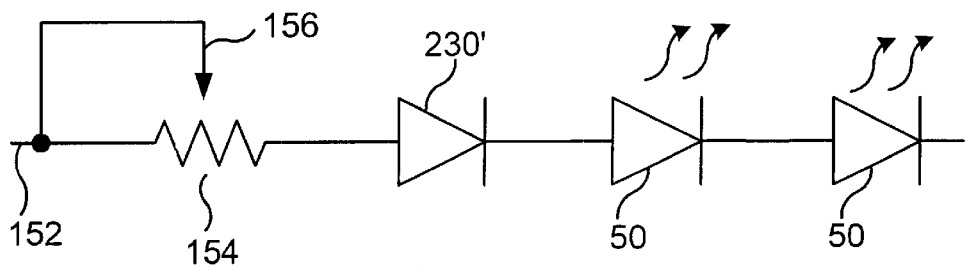
FIGS. 9A and 9B are circuit diagrams illustrating alternative implementations for providing temperature indicative data to a reflectometer.

Reference is now made to FIG. 9A wherein there is shown a circuit diagram illustrating a second temperature sensing mechanism useful in compensating for temperature. In this implementation, direct first order compensation for the variations in light intensity due to temperature is provided. One or two diodes 230' are connected in series with each other and the LEDs 50 between the square wave output on line 152 and the light level adjustment circuit 154 comprising the potentiometer 156. The diodes 230' are, like the diode 230, thermo-mechanically coupled to the LEDs 50. The voltage drop across the series connected diodes 230' with increased temperature results in the application of increased current to the LEDs 50. This increased current application provides a first order compensation for any diminishment in light intensity output from the LEDs 50 due to increasing temperature. For this series diode 230' compensation scheme, it is preferable to use a germanium or Schottky diode since the low forward voltage drop of these types is an advantage in controlling the sensitivity of the light-adjusting potentiometer 156. This series diode 230' compensation scheme may also be utilized in combination with the diode 230 sensor configuration illustrated in FIG. 7 to provide for improved temperature detection and compensation.

Figure 9B:
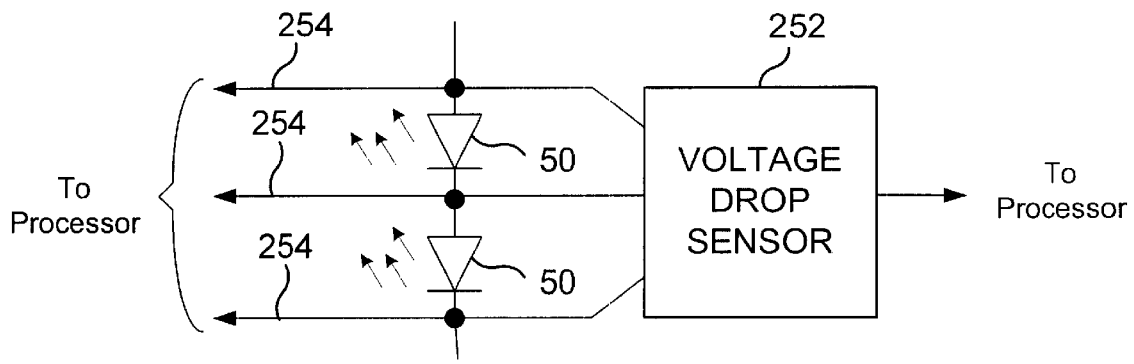

Reference is now made to FIG. 9B wherein there is shown a circuit diagram illustrating a third temperature sensing mechanism useful in compensating for temperature. In this implementation, a measurement of voltage drop is taken across one of the LEDs 50, across each of the LEDs, or across all of the LEDs. Using this measured instantaneous LED voltage drop, dynamic temperature compensation may be implemented to account for not only currently experienced temperature variations, but also long term degradation of the LEDs 50. In connection with the reflectometer 30/30' illustrated in FIG. 6A, a voltage drop detector 252 is provided to measure the voltage drop across one, each or all of the LEDs 50. The measured voltage drop may then be output through the external port connection for processing by the personal computer in accordance with the CV equation discussed above. In connection with the reflectometer 30/30' illustrated in FIG. 6B, on the other hand, a pair of analog taps 254 are taken off the anode/cathode leads of one, each or all of the LEDs 50 and input to the microprocessor. The analog to digital converter of the microprocessor then converts the measured voltages to digital signals, subtracts the values from each other and determines a resulting voltage drop for subsequent processing in accordance with the CV equation discussed above.

With reference now once again to FIGS. 7A and 7B, a fourth temperature sensing mechanism useful in compensating for temperature advantageously utilizes the synchronous detector DC level shifting diode 238 to measure temperature by sensing the voltage drop across the diode. In one configuration, the diode 238 may be thermo-mechanically coupled to the LEDs 50 to provide light source related temperature information for subsequent processing in accordance with the CV equation discussed above. In another configuration, the diode 238 may remotely located from any heat sources within the reflectometer 30/30' in order to provide ambient temperature information for subsequent processing in connection with evaluations which are dependent on knowing ambient (as opposed to light source) temperature. As an example, the biological and chemical reactions on the transdermal patch and/or strip are ambient temperature dependent. In order to calculate accurate incubation times, the diode 238 ambient temperature data may be processed to identify when is the proper time to take a reading.

Reference is now once again made to FIGS. 2A, 2B and 3. As discussed above, the reflectometer 30/30' is minimally affected by the external influence of light, induced noise, and temperature. Accordingly, the cylindrical shaped protruding nose 48 portion of the sensor head 32 need not necessarily provide a light-tight fit with the opening 14 in the transdermal patch 10 because leakage of ambient light, just like skin color, is compensated for by the synchronous detection feature. Internally, the alternating nature of the light source and detector circuit is not subject to DC drift. Furthermore, temperature compensation concerns have also been addressed through the use of temperature detection and compensation circuitry and processing as discussed above.

There are, however, other factors that can effect the accuracy of the color and shade reading. For example, the unsteady operation of the reflectometer 30 due, for example, to a rocking motion or other movement, may alter the illumination geometry at interface between the sensor head 32 and the transdermal patch 10. Another concern is the application of varying degrees of contact pressure between the reflectometer 30 and the transdermal patch 10. With specific respect to a hand-held device, it is vitally important that the routine to measure a repeatable peak hold on the output signal indicative of detected color and shade must be tolerant of vibrations and unsteady operation. To achieve this goal, data is sampled at a high enough rate such that as many data points as practical are input into an averaging routine. The technique for averaging these samples should be able to determine the correct reading within a few seconds and not be affected however by the time to take a reading.

Peak detection voltage stability is utilized as the test for insuring a repeatable result. If, for example, the detection voltage range is between 0.5 and 0.8 volts, then a peak detection voltage stability of 0.002 volts would provide for better than one percent resolution. A signal gain of five would result in a range of two and half to four volts, a range that is more compatible with a microprocessor having an analog to digital converter with a five volt supply.

Figures 10, 11:
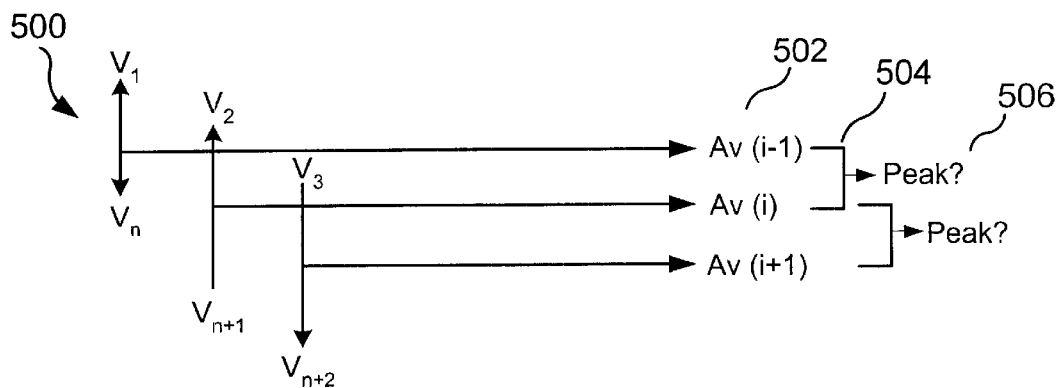
FIG. 10 is a diagram illustrating an exemplary operation of the peak hold detection algorithm used in processing a signal representative of the detected light.
FIG. 11 illustrates a lookup table which correlates a certain voltage indicative of detected target surface color and shade to a certain concentration of an analyte of interest.
Figure 13:
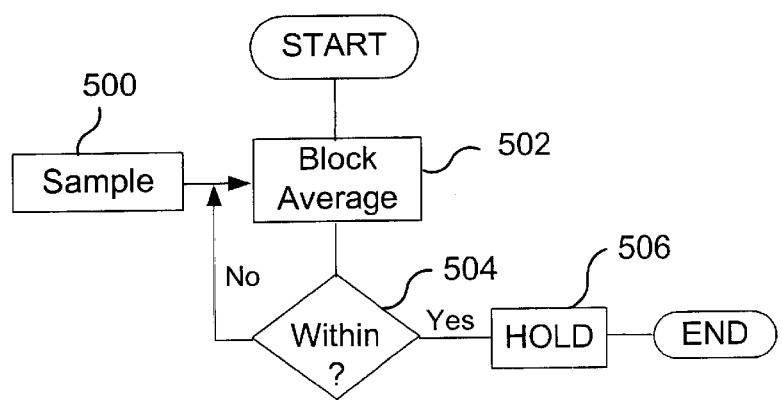
FIG. 13 is a flow diagram illustrating the peak hold detection algorithm used in processing a signal representative of the detected light.

Reference is now made to FIGS. 10 and 13 wherein there is shown an exemplary operation of the peak hold detection algorithm used in processing the DC voltage of the first analog signal representative of the detected reflected light at the target surface (and indicative of color and shade).

Raw data relating to uncompensated voltage is collected at a certain sampling rate (step 500). A moving block average (Av(i)) is then calculated for the last n samples (step 502). The moving block average Av(i) is then compared in step 504 to the most recent previous moving block average (Av(i−1)). If the deviation between the current moving block average Av(i) is less than a certain deviation voltage threshold from the most recent previous moving block average Av(i−1), then a steady state condition has been satisfied, and the current moving block average Av(i) is held as a peak value in step 506 for subsequent processing as the steady DC voltage indicative of the color and shade of the target surface. If the step 504 measured deviation exceeds the certain deviation voltage threshold, the process returns to step 502 to calculate a new current moving block average. The process continues sampling (step 500), calculating moving block averages (step 502), and comparing (step 504) until the determined deviation between the current moving block average Av(i) and the most recent previous moving block average Av(i−1) is less than a certain deviation voltage threshold.

The held peak value for the steady DC voltage is then processed first to adjust for the DC offset, then to correct for temperature, and then to adjust for color and/or batch calibration (if desired or necessary). The resulting compensated voltage directly relates to the color and shade of the reflectance off the target surface at standard conditions. The processor, by use of a stored lookup table or mathematical formula (based perhaps upon lookup table related data) that correlates a certain compensated voltage (indicative of target surface color and shade) to a certain analyte concentration, identifies an analyte concentration level output value. If the compensated voltage value falls between two rows in the lookup table, the end data points for the analyte concentration level are interpolated to produce an output. The user selection of reflectometer data (such as a manufacturing batch code for the transdermal patch 10 or testing strip 20) and type testing to be performed (for example, glucose versus cholesterol) identifies which one of a plurality of stored lookup tables should be considered by the processor in evaluating the compensated voltage indicative of target surface color and shade to determine the corresponding analyte concentration level output value. Other factors that may affect the calibration to an individual can also be affected by the choice of the lookup table. An example of a lookup table suitable for use in the reflectometer of the present invention is illustrated in FIG. 11.

In the context of the lookup table of FIG. 11 (or its equivalent mathematical formula), an example of the use of the reflectometer 30/30' to monitor glucose level is now presented. At 10:00 am, a pre-set audible alarm alerts the diabetic patient to take a glucose reading. A transdermal patch 10 is attached to the inside of the patient's forearm and the SELECT button is pressed, signaling the beginning of an incubation countdown period. After the period expires, another audible alarm having a distinct tone sequence alerts the patient that it is time to take a reading on the patch 10. The cylindrical shaped protruding nose 48 portion of the sensor head 32 is inserted within the opening 14 in the transdermal patch 10, and the READ button is pushed. After about one second of reading time, the first analog output signal has not yet reached a steady state condition (relative to the certain deviation voltage threshold). After about two seconds, steady state is reached and a DC offset adjusted, but temperature un-compensated, voltage is obtained with a value of 0.664 volts. This steady DC voltage is then presented to the processor as the first analog output signal for analysis. In addition, the temperature sensor diode 230 provides the third analog output signal with a value of 0.611 volts. In accordance with the temperature correction algorithm described above, a compensated voltage CV indicative of target surface color and shade is then calculated at 0.662 volts. If necessary, appropriate color and/or batch calibration adjustment may also be made. In the lookup table of FIG. 11 (or its equivalent mathematical formula), this compensated voltage correlates with a glucose level of between 140 and 180 mg/dL. Interpolation of these two end points produces a final result of 170.4 mg/dL. This glucose level is then rounded to the nearest whole number, and a final result of 170 mg/dL is displayed to the patient. The result is also stored in memory along with the date and time for future reference or to be downloaded to a computer as patient history.

Figure 12A:
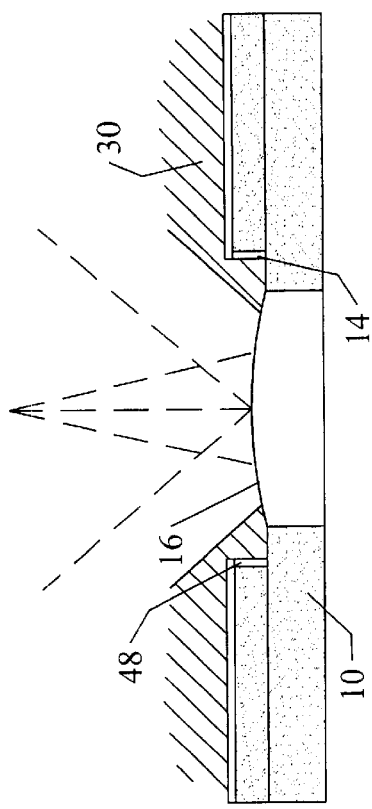
FIG. 12A is a cross-sectional view illustrating an improper engagement of the reflectometer sensor head and the transdermal patch due to excessive pressure.

Reference is now made to FIG. 12A wherein there is shown a cross-sectional view illustrating an improper engagement of the reflectometer and the transdermal patch. As mentioned previously, one of the factors that can affect the accuracy of the color and shade reading is the application of varying degrees of contact pressure between the reflectometer 30 and the transdermal patch 10. In this regard, it is noted that accurate measurement is dependent upon the target surface being in proper position. Uneven or excessive pressure can, however, distort (i.e., bow or ripple) the membrane 16 and move the target surface out of proper position. This effect is shown in exaggerated fashion in FIG. 12A. It has been observed that the result of increasing pressure applied to the patch by the reflectometer meter causes an increased reflectance signal due to the target surface deflecting toward the photo transistor. Furthermore, in some instances the membrane is inherently distorted or is distorted as a result of the biological and chemical reaction.

Figure 12B:
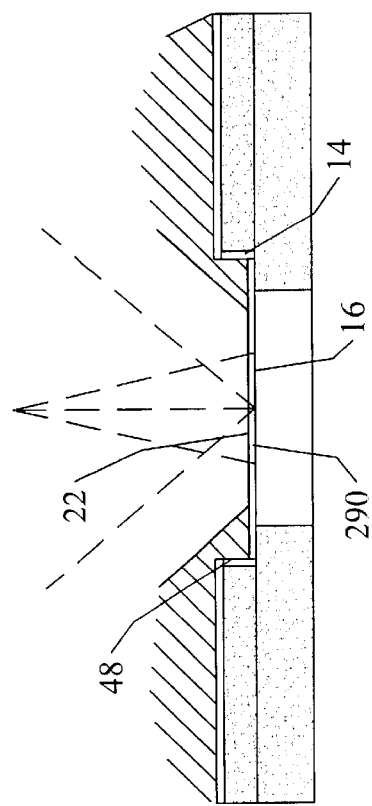
FIG. 12B is a cross-sectional view illustrating the use of a window on the nose portion of the reflectometer sensor head to ensure accurate positioning of the reflectometer with respect to the target surface.

Reference is now made to FIG. 12B wherein there is shown a cross-sectional view illustrating the use of a window 290 on the cylindrical shaped protruding nose 48 portion of the reflectometer sensor head 32. The window 290 serves to flatten out any existing distortions (bows, ripples and the like) in the membrane 16 and further render the measurement process relatively insensitive to variations in applied pressure. The target surface is accordingly accurately positioned for color and shade reading. The window 290 is transparent and is preferably made of a plastic or glass that exhibits a high transmissivity at the wavelength of the light source light used, in this case, that wavelength emitted by the LEDs 50. Additional requirements include durability and resistance to cleaning solutions and scratching. As an added benefit, the clear window 290 prevents dirt, dust and debris (which could reduce the sensitivity of the reflectometer and might also affect the calibration) from entering and accumulating within the sensor head.

Figure 12C:
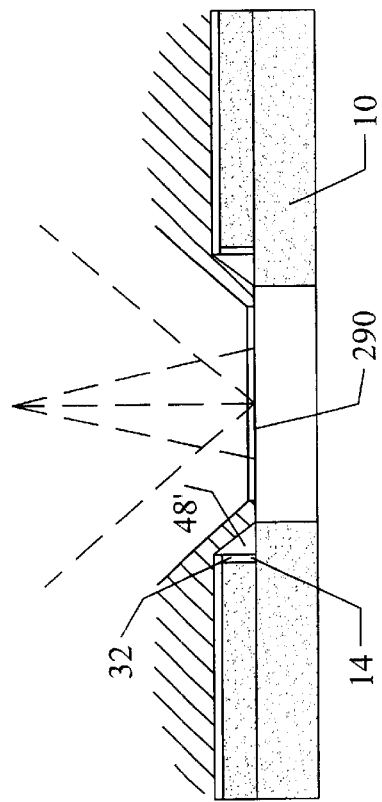
FIG. 12C is a cross-sectional view illustrating the use of a tapered nose portion for the reflectometer sensor head.

Reference is now made to FIG. 12C wherein there is shown a cross-sectional view illustrating the use of a tapered cylindrical shaped nose portion 48' of the reflectometer sensor head 32. As discussed above, the reflectometer 30/30' is substantially immune to the external influence of light. Accordingly, the nose portion 48/48' of the sensor head 32 need not necessarily provide a light-tight fit within the opening 14 in the transdermal patch 10. Leakage of ambient light, just like skin color, is compensated for by the included feedback signal and synchronous detection features. However, it is important, as illustrated in FIG. 12A, that the target surface be placed in proper position with respect to the head 48/48'. A cylindrical shaped sensor head 48 (like that shown in FIGS. 3, 12A and 12B) having a diameter nearly identical to the diameter of the circular opening in the transdermal patch 10 may not, in instances where the user is not careful, seat itself properly within the opening flush against the membrane. As an additional concern, the top surface of the transdermal patch may have an adhesive layer that could catch the nose making it more difficult to properly seat the nose within the patch opening. To assist the user in obtaining proper flush positioning of the reflectometer 30, the tapered shape of the cylindrical shaped nose portion 48' of the reflectometer sensor head 32 functions to find the opening in the patch 10 during insertion and facilitate proper placement of the reflectometer against the membrane. The window 290 is preferably recessed into the nose by its thickness to seal the opening in the sensor head and prevent the edge of the window from being caught and possibly damaged or removed during handling.

Reference is now once again made to FIGS. 6A and 6B. As mentioned previously, the reading process is initiated by having the user depress the SELECT button. This button signals the beginning of an incubation countdown period. It is recognized that the time required for completion of the biological and chemical processes that occur on the patch 10 or strip 20 may be temperature dependent. Thus, the processor of the reflectometer 30/30' utilizes the diode 238 to obtain information indicative of ambient temperature. When the SELECT button is activated, the processor uses the current ambient temperature information provided by the diode 238 to determine an incubation countdown period of sufficient length to insure completion of the biological and chemical processes on the patch 10 or strip 20 before signaling the user with an audible alarm indicating that it is time to take a reading.

Figure 14:
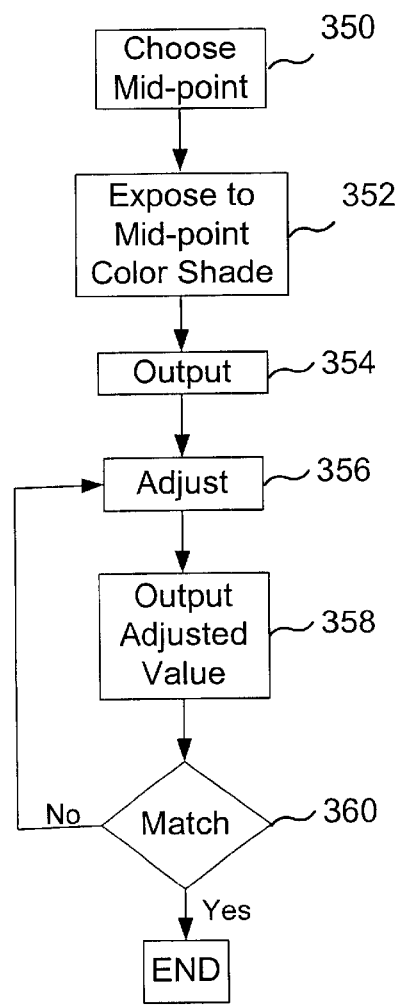
FIG. 14 is a flow diagram illustrating a process for performing a first order calibration of the reflectometer.

Reference is now made to FIG. 7 and to FIG. 14 wherein there is shown a flow diagram illustrating a process for performing a first order calibration of the reflectometer 30/30'. It is noted that this first order calibration must be performed at a controlled temperature (such as twenty-five degrees C). A point on the compensated voltage-analyte concentration curve (such as that represented by the lookup table of FIG. 11) is chosen in step 350 where it is preferred that the reflectometer be able to read most accurately. In most instances this point will be at or close to midrange on the curve. The reflectometer 30/30' is then exposed in step 352 to a standard color shade that corresponds with that chosen analyte concentration. A resulting compensated voltage or analyte concentration values is then output in step 354. The internal potentiometer 156 of the light level adjustment circuit 154 is then adjusted in step 356, with an adjusted compensated voltage being output in step 358. A test is then made in step 360 to determine whether the step 356 adjustment produced an adjusted compensated voltage in step 358 that matches the step 350 selected point on the compensated voltage-analyte concentration curve. If not, the process returns to perform steps 356, 358 and 360 over again. This is repeated until such time as the potentiometer 156 adjustment produces an adjusted compensated voltage that matches the compensated voltage at the selected point on the compensated voltage-analyte concentration curve. If this first order calibration process is performed with respect to each reflectometer 30/30', then each reflectometer will read exactly the same way at the midpoint, thus providing consistency in reflectometer operation from device to device.

Figure 15:
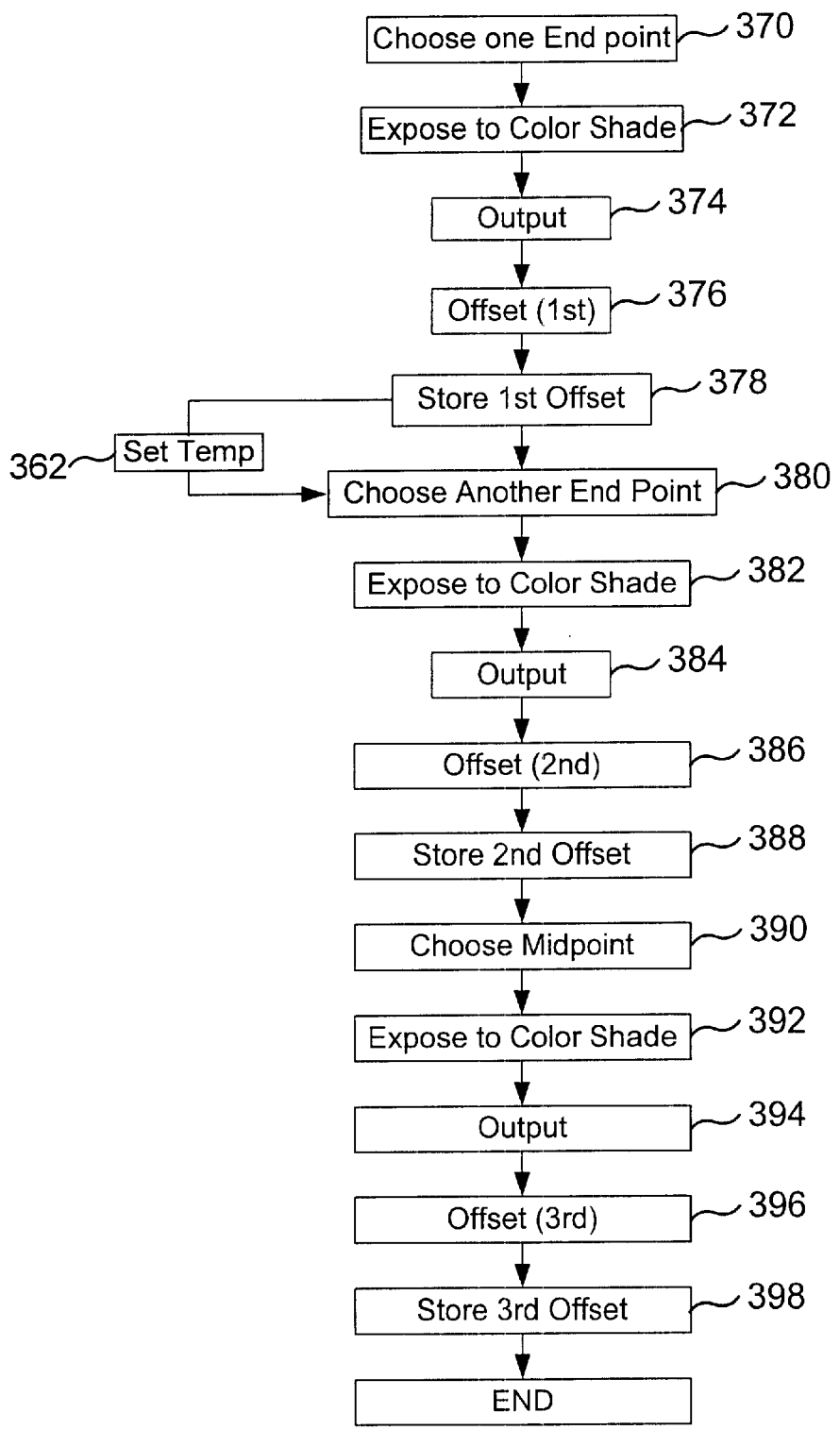
FIG. 15 is a flow diagram illustrating a process for performing a second and third order calibration of the reflectometer.

Reference is now made to FIGS. 6A and 6B and to FIG. 15 wherein there is shown a flow diagram illustrating a process for performing a second order calibration of the reflectometer 30/30'. It is noted that this second order calibration must be performed at a controlled temperature (such as twenty-five degrees C). A point on one end of the compensated voltage-analyte concentration curve (such as that represented by the lookup table of FIG. 11) is chosen in step 370. The reflectometer 30/30' is then exposed in step 372 to a standard color shade that corresponds with that chosen analyte concentration. A resulting compensated voltage value is then output in step 374. A first end point offset between the output compensated voltage value and the compensated voltage at the selected end point on the compensated voltage-analyte concentration curve is then determined in step 376 and stored (in non-volatile memory) by the processor in step 378. At this point, a measurement is also made of the voltage drop across the temperature sensor 128 diode 230 and stored (in non-volatile memory) by the processor in step 362. A point on the other end of the compensated voltage-analyte concentration curve is then chosen in step 380. The reflectometer 30/30' is then exposed in step 382 to a standard color shade that corresponds with that chosen analyte concentration. A resulting compensated voltage value is then output in step 384. A second end point offset between the output compensated voltage value and the compensated voltage at the selected end point on the compensated voltage-analyte concentration curve is then determined in step 386 and stored (in non-volatile memory) by the processor in step 388. A point in the middle of the compensated voltage-analyte concentration curve is then chosen in step 390. The reflectometer 30/30' is then exposed in step 392 to a standard color shade that corresponds with that chosen analyte concentration. A resulting compensated voltage value is then output in step 394. A mid-point offset between the output compensated voltage value and the compensated voltage at the selected end point on the compensated voltage-analyte concentration curve is then determined in step 396 and stored (in non-volatile memory) by the processor in step 398. The stored first and second end point offsets and mid-point offset may then be taken into account by the processor in using the stored lookup table (or mathematical algorithm), which correlates a certain compensated voltage (indicative of read target surface color and shade) to a certain analyte concentration, to identify an analyte concentration level output value. Although not specifically illustrated, more than two or three points on the curve may be selected for second order calibration in order to provide for more accurate operation.

It is noted that the second order calibration process of FIG. 15 may be performed multiple times on a single meter in situations where the meter is likely be utilized to make readings for different types of tests (for example, glucose and cholesterol). In such a case, the reflectometer 30/30' is programmed with plural stored lookup tables (or mathematical algorithms) which each correlate a certain compensated voltage (indicative of read target surface color and shade) to a certain analyte concentration. The reflectometer must be calibrated to applicable data for each of those tests in order to ensure proper performance.

It is recognized that the color indications developed on the transdermal patches or strips may vary between manufacturing batches. One way to handle this concern is to code each batch in accordance with its color indications. Each meter is then preprogramed with the batch code designations and appropriate offsets at the first and second end points and mid-point. In situations where preprograming in this manner is not possible, the process illustrated in FIG. 15 may be performed by the patient (as opposed to at the factory) with respect to each batch of transdermal patches or strips used. To support this patient batch code (third order) calibration process, each batch of transdermal patches or strips would include three standard color shades, with each shade corresponding with a certain analyte concentration as measured by that batch. After completion of the process, stored first and second end point offsets and mid-point offset relating to batch variation may then be taken into account by the processor in using the stored lookup table (or mathematical algorithm), which correlates a certain compensated voltage (indicative of read target surface color and shade) to a certain analyte concentration, to identify an analyte concentration level output value.

Figure 16:
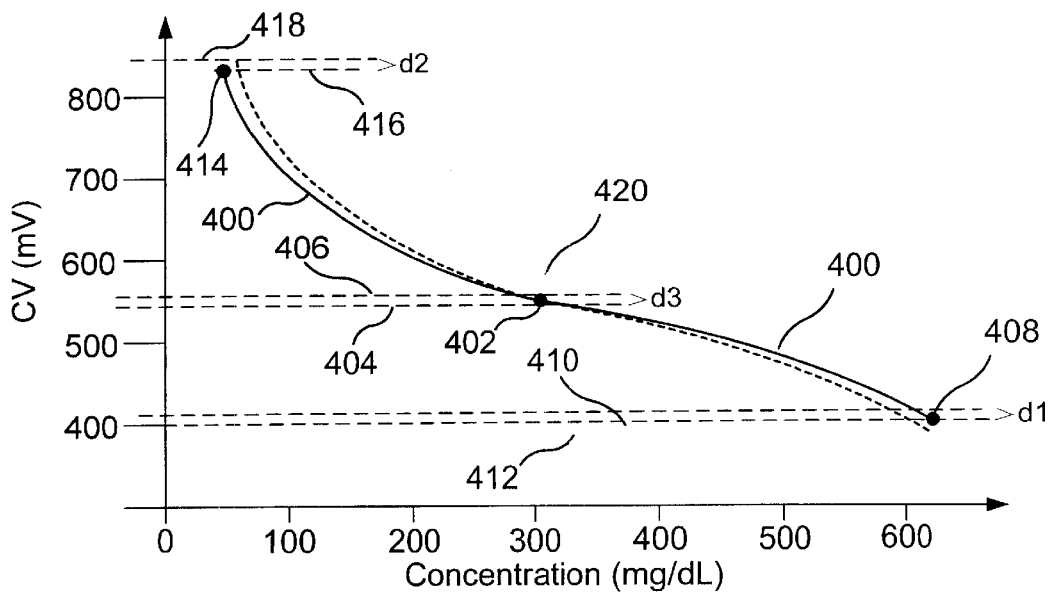
FIG. 16 is a graph illustrating an exemplary compensated voltage-analyte concentration curve and the affect thereon of the first, second and third order calibration processes of FIGS. 14 and 15, respectively.

Reference is now made to FIG. 11 and to FIG. 16 wherein there is shown a graph illustrating an exemplary compensated voltage-analyte concentration curve 400 and the affect thereon of the first and second order calibration processes of FIGS. 14 and 15, respectively. The curve 400 represents the relationship between a certain measured compensated voltage (on the y-axis) and a corresponding analyte concentration (on the x-axis). More precisely, the curve 400 presents the specific compensated voltage-analyte concentration relationship illustrated in FIG. 11.

Turning first to the first order calibration process of FIG. 14, a mid-point 402 on the curve 400 of FIG. 16 is selected (in this instance representing an analyte concentration of 300 mg/dL). The reflectometer is then exposed to a standard color shade that corresponds with that chosen analyte concentration. Instead of producing a corresponding expected compensated voltage 404 reading (in this instance comprising 550 mV), the reflectometer reports a different compensated voltage 406. Appropriate potentiometer 156 adjustment is then performed in order to bring the reflectometer reported compensated voltage 406 into a matching relationship with the expected compensated voltage 404. Storage is also made at this point of the voltage drop across the temperature sensor 128 diode 230.

Turning next to the second order calibration process of FIG. 15, a first end point 408 on the curve 400 of FIG. 16 is selected (in this instance representing an analyte concentration of 625 mg/dL). The reflectometer is then exposed to a standard color shade that corresponds with that chosen analyte concentration. Instead of producing a corresponding expected compensated voltage 410 reading (in this instance comprising 400 mV), the reflectometer reports a different compensated voltage 412. The offset d1 between the expected compensated voltage 410 and the reflectometer reported compensated voltage 412 is determined and stored. A second end point 414 on the curve 400 is selected (in this instance representing an analyte concentration of 55 mg/dL). The reflectometer is then exposed to a standard color shade that corresponds with that chosen analyte concentration. Instead of producing a corresponding expected compensated voltage 416 reading (in this instance comprising 850 mV), the reflectometer reports a different compensated voltage 418. The offset d2 between the expected compensated voltage 416 and the reflectometer reported compensated voltage 418 is determined and stored. A mid-point 420 on the curve 400 is selected (in this instance representing an analyte concentration of 300 mg/dL). The reflectometer is then exposed to a standard color shade that corresponds with that chosen analyte concentration. Due to the first order calibration provided above, the reflectometer should produce the expected compensated voltage 404 reading (in this instance comprising 550 mV). If it does not, then the first and second order calibration processes should be performed again. In the event the reflectometer is being programed for use in connection with different types of tests (for example, glucose and cholesterol), the reflectometer likely will not produce the expected compensated voltage 404 reading. Rather, the reflectometer reports a different compensated voltage 406. The offset d3 between the expected compensated voltage 404 and the reflectometer reported compensated voltage 406 is determined and stored. The stored first and second end point offsets d1 and d2 and mid-point offset d3 may then be taken into account by the processor in using the stored lookup table (see, FIG. 11) or mathematical formula when processing a detected compensated voltage (indicative of read target surface color and shade) to identify an analyte concentration level output value. The result of this second order calibration is, in effect, to produce an adjusted compensated voltage-analyte concentration curve 400' (illustrated with a dashed line) for each type of test that takes into account the tolerances of the specific reflectometer 30/30' at issue. In processing the reflectometer 30/30' detected compensated voltage at points on the curve 400 (look-up table of FIG. 11) between the end-points 408 and 414, an interpolation of the appropriate d1, d2 or d3 offset may be calculated (along with any interpolation necessary to make the calculation between the data points in the look-up table or mathematical formula) making a final determination of an analyte concentration level output value. The foregoing process may then be repeated by the patient in order to calculate additional d1, d2 and d3 offsets and thus produce another adjusted compensated voltage-analyte concentration curve 390' (illustrated with a dashed line) for each batch of patches or strips.

Figure 17:
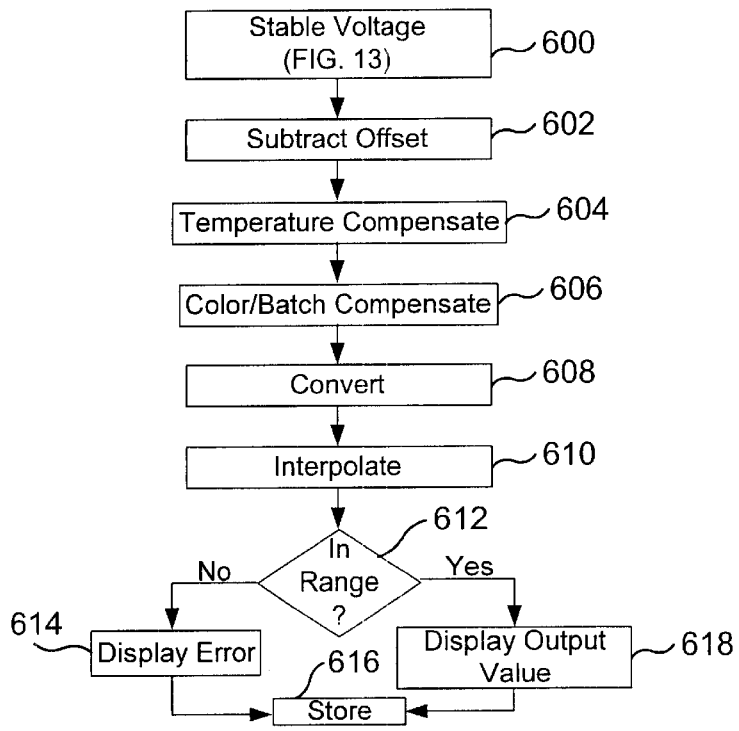
FIG. 17 is a flow diagram illustrating a process for converting an input voltage indicative of read color shade into a concentration value output.

Reference is now made to FIG. 17 wherein there is shown a flow diagram illustrating a process for converting an input voltage indicative of read color shade into a concentration value output. The illustrated process not only accounts for any temperature considerations in generating the compensated voltage, but also accounts for any interpolations required by the second order calibration offsets (see, FIG. 15) and the calculation between the data points in the look-up table (see, FIG. 11). In step 600, a stable output voltage indicative of color and shade has been determined (see, FIG. 13). If any DC offsets affecting the accuracy of stable output voltage are present (such as that provided with respect to the synchronous detector), these offset(s) are subtracted from the stable output voltage in step 602. Next, in step 604, the offset adjusted stable output voltage is processed using the equation discussed above to compensate for variations in light source intensity due to temperature and produce a compensated voltage (CV). The compensated voltage is then processed in step 606 to make any needed adjustments relating to second order color calibration and third order batch code calibration (see, FIGS. 15 and 16). A lookup table (or mathematical formula) is then used to convert the color (batch code) calibration adjusted compensated voltage in step 608 to a concentration level. Any necessary interpolations to the determined concentration level are then made in step 610. A determination is then made in step 612 as to whether the (interpolated) determined concentration level is within an acceptable anticipated range for the particular test being made. If not, an error message is displayed in step 614, and record of the error is stored in step 616 along with a date and time of day. If so, the (interpolated) determined concentration level is displayed in step 618, and record of the level is stored in step 616 along with a date and time of day.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A reflectometer, comprising:
   a modulated light source for emitting light to illuminate a target surface which possesses a certain color and shade of color;
   an optical detector for detecting light that is reflected from the target surface and generating a first output indicative of detected light;
   means for processing the first output to generate a feedback signal for application to the optical detector to compensate for any shift in the first output resulting from the detection of ambient light by the optical detector, and differentially amplify the first output to generate a second output; and
   a detector for synchronously demodulating the second output to generate a substantially steady DC output voltage that is indicative of the color or shade of color at the target surface.

2. The reflectometer as in claim 1 wherein the modulated light source emits light having an intensity that varies with changes in temperature, the reflectometer further comprising:
   a temperature sensor thermo-mechanically coupled to the modulated light source, the sensor generating a third output indicative of temperature of the modulated light source; and
   means for mathematically correcting the substantially steady DC output voltage in accordance with the third output to account for detected changes in modulated light source temperature.

3. The reflectometer as in claim 2 wherein the modulated light source comprises at least one light emitting diode, and wherein the temperature sensor comprises a diode means having an operating characteristic substantially complementing that of the light emitting diode.

4. The reflectometer as in claim 1 wherein the modulated light source emits light having an intensity that varies with changes in temperature, the reflectometer further comprising:
   a temperature compensator thermo-mechanically coupled to the modulated light source; and
   means for having the temperature compensator control operation of the modulated light source to counteract for any variations in light intensity due to changes in modulated light source temperature.

5. The reflectometer as in claim 4 wherein the modulated light source comprises at least one light emitting diode, wherein the temperature compensator comprises a diode, and wherein the means for having comprises a series electrical connection of the diode with the light emitting diode.

6. The reflectometer as in claim 1 wherein the modulated light source emits light having an intensity that varies with changes in voltage drop across the modulated light source, the reflectometer further comprising:
   a sensor for measuring voltage drop across the modulated light source during target surface illumination; and
   means for mathematically correcting the substantially steady DC output voltage in accordance with the measured voltage drop to account for variations in light intensity.

7. The reflectometer as in claim 1 wherein the optical detector comprises:
   a photo transistor for receiving and detecting light that is reflected from the target surface and generating a first differential signal;
   a transistor for setting the quiescent operating point and generating a second differential signal; and
   means for connecting the photo transistor and transistor at a common emitter connection in a differential configuration.

8. The reflectometer as in claim 7 further comprising a current mirror for supplying fixed constant current into the common emitter connection between the differentially connected photo transistor and transistor.

9. The reflectometer as in claim 7 wherein the means for processing processes the second differential signal to generate the feedback signal for application to the photo transistor to bias the photo transistor to the quiescent operating point.

10. The reflectometer as in claim 9 wherein the means for processing comprises an integrator for comparing the second differential signal to a reference voltage and integrating a result of the comparison to generate the feedback signal, wherein the feedback signal is indicative of an error between the quiescent operating point and a shift caused by DC ambient light detected at the photo transistor.

11. The reflectometer as in claim 1 wherein the modulated light source comprises:
   at least two light emitting diodes; and
   means for mounting the light emitting diodes each at an orientation angle away from an orientation angle of the optical detector so as to provide for substantially uniform illumination of the target surface with minimal specular reflection to the optical detector.

12. The reflectometer as in claim 11 wherein the two light emitting diodes are of different color.

13. The reflectometer as in claim 1 wherein the detector for synchronously demodulating comprises a full wave synchronous detector producing a DC voltage proportional to the peak to peak voltage of the second output signal.

14. The reflectometer as in claim 1 further including a hand held case for containing the modulated light source, optical detector, amplifier, and synchronous detector.

15. The reflectometer as in claim 14 wherein the target surface comprises a color developing membrane of a transdermal patch, and the hand held case includes a reader head adapted for mating with the color developing membrane of the transdermal patch.

16. The reflectometer as in claim 15 wherein the transdermal patch includes an opening exposing the color developing membrane to view, and the reader head includes a nose configured for insertion into the transdermal patch opening.

17. The reflectometer as in claim 16 wherein the nose of the reader head includes a transparent window for flattening the color developing membrane when the reader head is inserted into the transdermal patch opening.

18. The reflectometer as in claim 16 wherein the opening in the transdermal patch has a certain size and shape, and wherein the nose configuration of the reader head has a complementary size and shape.

19. The reflectometer as in claim 16 wherein the opening is circular, and wherein the nose configuration has a cylindrical shape adapted to fit within the circular opening.

20. The reflectometer as in claim 19 wherein the cylindrical shape of the nose configuration is tapered to allow the reader head to find the circular opening.

21. The reflectometer as in claim 1 further including a desk top case for containing the modulated light source, optical detector, amplifier, and synchronous detector.

22. The reflectometer as in claim 21 wherein the target surface comprises a color developing testing strip, and the desk top case includes a reader site adapted for constraining the color developing test strip.

23. The reflectometer as in claim 1 wherein the target surface color shade is indicative of a certain measurable quantity or quality, the reflectometer further comprising a processor for converting the steady DC voltage indicative of the color or shade of color at the target surface into a corresponding quantity or quality measurement.

24. The reflectometer as in claim 23 further comprising a stored look-up table or mathematical formula correlating steady DC voltage values to corresponding quantity or quality measurements, the processor consulting the look-up table or mathematical formula in making its conversion.

25. The reflectometer as in claim 24 wherein the measurable quantity or quality comprises an analyte concentration.

26. The reflectometer as in claim 25 wherein the analyte concentration comprises either a glucose level or a cholesterol level.

27. The reflectometer as in claim 1 wherein the modulated light source emits light having an intensity that varies with changes in temperature, and wherein the target surface color shade is indicative of a certain measurable quantity or quality, the reflectometer further comprising:

a sensor generating a temperature signal indicative of light source temperature; and a processor for correcting the steady DC voltage indicative of the color or shade of color at the target surface in accordance with the temperature signal to generate a compensated DC voltage, and for converting the compensated DC voltage into a corresponding quantity or quality measurement.

* * * * *